United States Patent [19]

Cipolli et al.

[11] Patent Number: 5,403,877
[45] Date of Patent: Apr. 4, 1995

[54] SALTS OF TRIAZINE DERIVATIVES WITH OXYGENATED ACIDS OF PHOSPHORUS AND THEIR USE IN SELF-EXTINGUISHING POLYMERIC COMPOSITIONS

[75] Inventors: Roberto Cipolli, Novara; Enrico Masarati, Castelnuovo Valtidone; Gilberto Nucida, San Giuliano Milanese; Roberto Oriani, Milan; Mario Pirozzi, San Donato Milanese, all of Italy

[73] Assignee: Ministero Dell'Universita E Della Ricerca Scientifica E. Tecnologica, Rome, Italy

[21] Appl. No.: 108,033

[22] Filed: Aug. 18, 1993

Related U.S. Application Data

[62] Division of Ser. No. 727,710, Jul. 10, 1991.

[30] Foreign Application Priority Data

Jul. 11, 1990 [IT] Italy ................ 20919 A/90

[51] Int. Cl.6 .................. C08K 3/3492; C08K 3/32
[52] U.S. Cl. .................... 524/100; 524/86; 524/97; 524/415; 524/416
[58] Field of Search ............... 524/97, 100, 415, 416, 524/86

[56] References Cited

U.S. PATENT DOCUMENTS

| | | | |
|---|---|---|---|
| 4,201,705 | 5/1980 | Halpern et al. | 521/90 |
| 4,504,610 | 3/1985 | Fontanelli et al. | 524/416 |
| 4,656,200 | 4/1987 | Clubley et al. | 521/108 |
| 4,727,102 | 2/1988 | Scarso | 524/416 |
| 4,812,499 | 3/1989 | Cipriani et al. | 524/416 |
| 4,879,327 | 11/1989 | Poisson et al. | 524/93 |
| 5,153,245 | 10/1992 | Cipolli et al. | 524/416 |
| 5,198,483 | 3/1993 | Gainer | 524/100 |
| 5,200,445 | 4/1993 | Cipolli et al. | 524/100 |
| 5,210,120 | 5/1993 | Cipolli et al. | 524/100 |
| 5,223,560 | 6/1993 | Cipolli et al. | 524/100 |
| 5,225,463 | 7/1993 | Cipolli et al. | 524/100 |

FOREIGN PATENT DOCUMENTS

| | | |
|---|---|---|
| 0149480 | 7/1985 | European Pat. Off. . |
| 0286478 | 10/1988 | European Pat. Off. . |
| 0415372A2 | 3/1991 | European Pat. Off. . |

OTHER PUBLICATIONS

European Search Report, EP91111506, The Hague, Jan. 17, 1992.

*Primary Examiner*—Kriellion S. Morgan
*Attorney, Agent, or Firm*—Morgan & Finnegan

[57] ABSTRACT

This invention relates to salts of triazine derivatives with oxygenated acids of phoshporus, having general formula (I):

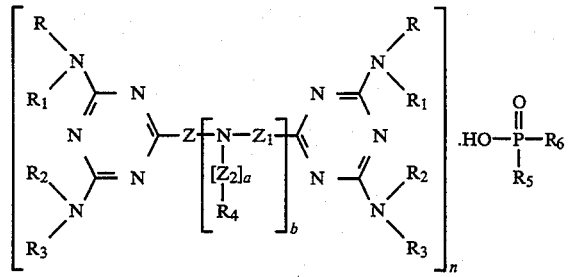

obtained by salification, with an acid containing phosphorus, of polycondensates of 2,4,6-triamino-1,3,5-triazine.

The compounds having the general formula (I) are particularly used as flame-resistant additives.

15 Claims, No Drawings

SALTS OF TRIAZINE DERIVATIVES WITH OXYGENATED ACIDS OF PHOSPHORUS AND THEIR USE IN SELF-EXTINGUISHING POLYMERIC COMPOSITIONS

This is a divisional of co-pending application Ser. No. 07/727,710, filed Jul 10, 1991.

FIELD OF THE INVENTION

The present invention relates to salts of triazine derivatives with oxygenated acids of phosphorus More specifically the present invention relates to salts of triazine derivatives with oxygenated acids of phosphorus and their use in the preparation of self-extinguishing polymeric compositions based on thermoplastic polymers or on polymers having elastomeric properties, particularly olefinic polymers or copolymers.

BACKGROUND OF THE INVENTION

Various solutions are known in the art for reducing or eliminating the combustion of polymers. Some of these solutions are based on the use of metals derivatives, especially antimony, bismuth or arsenic, combined with partially halogenated and thermically unstable organic compounds such as paraffinic chlorinated waxes. Other solutions are based on the use of substances capable of producing intumescence. The formulations of products using such substances are generally constituted of the polymer and at least three main additives: one essentially phosphorated, the aim of which is to give, in combustion, an impermeable semisolid glassy layer consisting essentially of polyphosphoric acid and to activate the intumescence process; a second additive containing nitrogen which acts as a foaming agent, and a third additive containing carbon, which provides the carbon necessary for forming a char layer between the polymer and the flame.

Examples of such formulations are those referred to in the following patents: U.S. Pat. No. 3,810,862 (Phillips Petroleum Co.) based on melamine, pentaeritritol and ammonium polyphosphate, U.S. Pat. No. 4,727,102 (Vamp S.r.l.) based on melamine cyanurate a hydroxyalkyl derivative of isocyanuric acid, and ammonium polyphosphate; and in the published patent application WO 85/05626 (Plascoat U.K. Ltd) based on various phosphorus and nitrogen derivatives, including, in particular, a combination of melamine phosphate, pentaerythritol and ammonium polyphosphate. In more recent formulations, an organic compound containing nitrogen, generally an aminoplastic resin obtained by the condensation of urea, melamine or dicyandiamide with formaldehyde, has been used together with an organic or inorganic phosphorous derivative. Examples of formulations with two additives are referred to in patents U.S. Pat. No. 4,504,610 (Montedison Spa) based on oligomeric derivatives of 1,3,5-triazine and ammonium polyphosphate, and EP 14.463 (Montedison Spa), based on organic compounds chosen among benzylguanamine and reaction products of aldehydes and various cyclic nitrogen-substituted compounds, in particular benzylguanamine and formaldehyde copolymers, and of ammonium polyphosphate. It is also possible to obtain self-extinguishing compositions by using mono component additives, containing both nitrogen and phosphorus in the organic molecule as described in U.S. Pat. No. 4,201,705 (Borg-Warner Corp.)

These flame-retardant, intumescent systems give the polymer in which they are contained the property of forming a carbon residue following combustion or contact with a flame. The flame-retardant systems of this kind show numerous advantages: non-corrosion of the machinery used to process the polymers, lower smoke emission compared to systems containing metal derivatives and halogenated hydrocarbons and, above all, the possibility of giving the polymers satisfactory flame-retardant properties using a lower quantity of additive, consequently avoiding a high decrease in the mechanical properties of the polymers.

The Applicant has now discovered that high flame-retardant properties can be conferred to polymers by using mono-components additives which allow to obtain polymeric compositions free of ammonium or amine phosphates and/or phosphonates, or excellent flame-retardant properties by using, with the above additives, a much lower quantity of ammonium or amine phosphates and/or phosphonates than that used in traditional methods.

The Applicant has also discovered that these excellent results can be obtained by using phosphorus-nitrogen containing products having a simple structure, based on polycondensates of 2,4,6-triamino-1,3,5-triazine salified with a phosphorus containing acid. The new additives, moreover, show good stability to heat, thus maintaining a high flame-retardant activity even when the polymeric compositions in which they are contained are processed under heat.

As said before, saline derivatives of 2,4,6-triamino-1,3,5-triazine (melamine) containing phosphors, are known (published patent application WO 85/05626) which can be used as co-additives for self-extinguishing compositions in various polymeric matrices, particularly polyolefines. These compounds, such as the melamine phosphate and melamine pyrophosphate, in order to act as flame-retarardant agents, need the presence of other additives, mainly of a compound containing carbon which is necessary for forming an insulating char layer, such as a polyol (pentaerythritol, dipentaerythritol, tripentaerythritol).

On the contrary, the compounds of the present invention are used in formulations of polymeric materials as intumescent char-forming flame-retardant additives without the help of other components.

The polymeric compositions containing the phosphorusnitrogen. products of the present invention, also have the advantage of emitting a very moderate and not darkening smoke emission in the event of fire.

DESCRIPTION OF THE INVENTION

The present invention consequently concerns salts having the general formula (I):

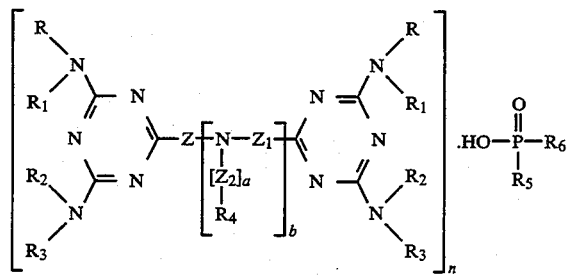

where:

the radicals from R to $R_3$, either alike or different, and which can also have different meanings for each triazine ring, are: H; $C_1$-$C_{18}$ alkyl; $C_2$-$C_8$ alkenyl; $C_6$-$C_{16}$ cycloalkyl or alkylcycloalkyl, possibly substituted with an oxydrilic or $C_1$-$C_4$ hydroxy alkyl function; [on the condition that the bivalent or polyvalent radicals, defined below, do not belong to the general formulas (III) and (XII) respectively, and the radicals $R_5$ and $R_6$, defined below, are different from H and OH respectively;]

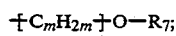

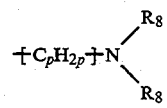

with:
m = integer comprised between 2 and 8, preferably between 2 and 4;
p = integer comprised between 2 and 6;
$R_7$ = H; $C_1$-$C_8$ alkyl, preferably H or $C_1$-$C_4$ alkyl; $C_2$-$C_6$ alkenyl;

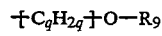

where q is an integer comprised between 1 and 4 and $R_9$ is H or $C_1$-$C_4$ alkyl; $C_6$-$C_{12}$ cycloakyl or alkylcycloakyl; the $R_8$ radicals, either alike or different, are: H; $C_1$-$C_8$ alkyl; $C_2$-$C_6$ alkenyl; $C_6$-$C_{12}$ cycloakyl or alkylcycloakyl; $C_1$-$C_4$ hydroxyalkyl; [on the condition that the bivalent or polyvalent radical, defined below, do not belong to the general formulas (III) and (XII) respectively, and the radicals $R_5$ and $R_6$, defined below, are different from H and OH respectively;] or the group:

is replaced by an heterocyclic radical linked to the alkyl chain by the nitrogen atom and optionally containing another hetero atom preferably chosen from O, S, N; or in the general formula (I) at least one of the groups:

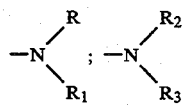

is replaced by a heterocyclic radical linked to the triazine chain by the nitrogen atom and optionally containing another hetero atom chosen preferably from O, S, N;

a is 0 or 1
b is 0 or an integer comprised between 1 and 5;
$R_4$ is hydrogen or:

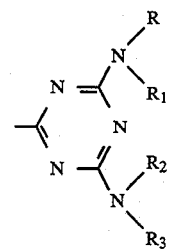

and its meaning can vary within each repetition unit; when b is 0, Z is a bivalent radical included in one of the following formulae:

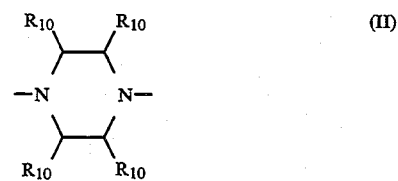

where the $R_{10}$ radicals, either alike or different, are hydrogen or $C_1$-$C_4$ alkyl;

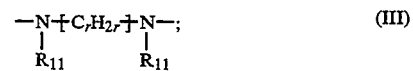

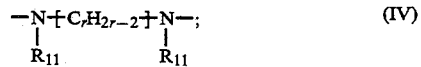

where r is an integer comprised between 2 and 14; $R_{11}$ is hydrogen; $C_1$-$C_4$ alkyl; $C_2$-$C_6$ alkenyl; $C_1$-$C_4$ hydroxyalkyl;

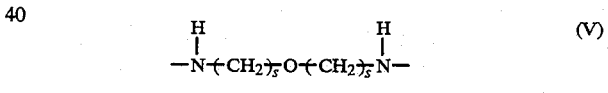

where s is an integer comprised between 2 and 5 and t is an integer comprised between 1 and 3;

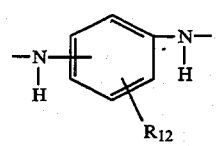

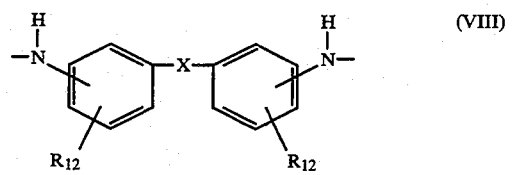

where:
X is a C—C bond; O; S; S—S; SO; $SO_2$; NH; $NHSO_2$; NHCO; N=N; $CH_2$;
$R_{12}$ is hydrogen; hydroxy radical; $C_1$-$C_4$ alkyl; $C_1$-$C_4$ alcoxyle;

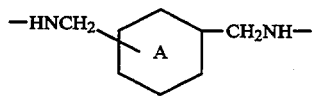 (IX)

where A can be a saturated or unsaturated cycle;

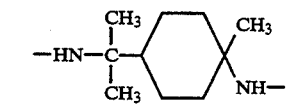 (X)

 (XI)

where s has the previously defined meaning;
when b is an integer comprised between 1 and 5 the group:

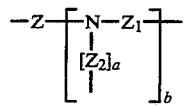

is a polyvalent radical included in one of the following formulae:

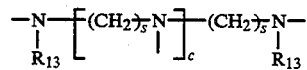 (XII)

where:
$R_{13}$ is hydrogen or $C_1$-$C_4$ alkyl;
c is an integer comprised between 1 and 5;
indexes s, either alike or different, have the above defined meaning;

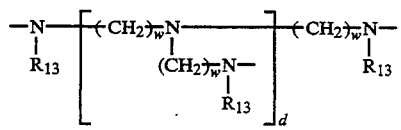 (XIII)

where:
$R_{13}$ has the previously defined meaning;
w is an integer comprised between 2 and 4;
d is either 1 or 2;
n is a number from 0 to 3, particularly from 0.2 to 2.5;
$R_5$ is H, OH, —O—$C_1$-$C_8$ alkyl; —O—$C_6$-$C_{12}$ aryl, optionally substituted with a $C_1$-$C_8$ alkyl; $C_7$-$C_{12}$ aralkyl, optionally substituted with a $C_1$-$C_4$ alkyl; $C_1$-$C_4$ alkyl, optionally substituted with a carboxylic group; $C_6$-$C_{12}$ aryl;
$R_6$ is H, OH, —O—$C_1$-$C_8$ alkyl; —O—$C_6$-$C_{12}$aryl; $C_1$-$C_4$ alkyl; $C_6$-$C_{12}$ aryl;
$R_6$ also is:

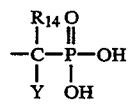

where:
$R_{14}$ is H or $C_1$-$C12$ alkyl;
Y is OH or $R_{14}$;

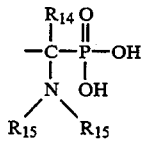

where:
$R_{14}$ has the previously defined meaning, and the $R_{15}$ radicals, either alike or different, are H or $C_1$-$C_4$ alkyl;
or the group:

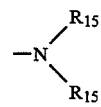

is replaced by a heterocyclic radical linked to the carbon atom by the nitrogen atom and optionally containing another heteroatom chosen preferably among O, S, N;

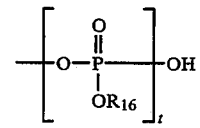

where:
$R_{16}$ is H or $C_1$-$C_8$ alkyl; and t has the previously defined meaning;

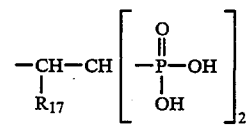

where:
$R_{17}$ is H or OH;

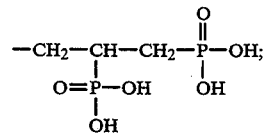

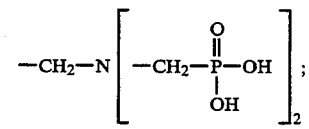

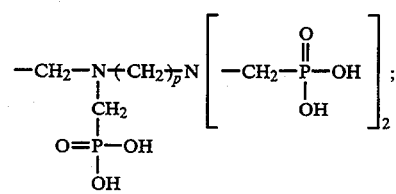

-continued

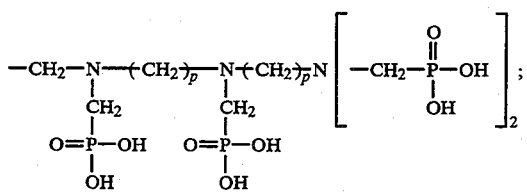

where:
p has the previously defined meaning;
or
R₅ and R₆ together may form a cyclic structure having formula:

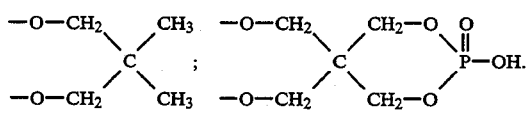

Also the compounds having asymmetrical structure, in the sense that any radical from R to R₃ may have different meanings on any triazine ring, belong to the general formula (I).

Examples of radicals from R to R₃ in formula (I) are: methyl; ethyl; propyl; isopropyl; n-butyl; isobutyl; tert-butyl; n-pentyl; isopentyl; n-hexyl; tert-hexyl; octyl; tert-octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl: 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyhethyl; 3-ethoxypropyl; 4-ethoxybuthyl; 3-propoxypropyl; 3-butoxypropyl; 4-butoxybuthyl; 4-isobutoxybuthyl; 5- propoxypentyl; 2-cyclohexyloxyethyl; 2-ethenyloxyethyl; 2-(N,N-dimethylamino)ethyl; 3-(N,N-dimethylamino)propyl; 4-(N,N-dimethylamino)buthyl; 5-(N,N-dimethylamino)pentyl; 4-(N,N-diethylamino)buthyl; 5-(N,N-diethylamino)pentyl; 5-(N,N-diisopropylamino)pentyl; 3-(N-ethylamino)propyl; 4-(N-methylamino)buthyl; 4-(N,N-dipropylamino)buthyl; 2-(N,N-diisopropylamino)ethyl; 6-(N-hexenylamino)hexyl; 2-(N-ethenylamino)ethyl; 2-(N-cyclohexylamino)ethyl; 2-(N-2-hydroxyethylamino)ethyl 2-(2-hydroxyethoxy)ethyl; 2-(2-methoxyethoxy)ethyl; 6-(N-propylamino) hexyl; etc..

Examples of heterocyclic radicals which can replace the groups:

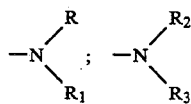

are: aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine, 2-ethylpiperazine; 2,5-diethylpiperazine; etc..

Examples of heterocyclic radicals which can replace the group:

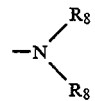

are: aziridine; pyrrolidine; piperidine; morpholine; thiomorpholine; piperazine; 4-methylpiperazine; 4-ethylpiperazine; etc..

Examples of divalent -Z- radicals are those obtained from the following diamino compounds by eliminating one hydrogen atom from any amino group: piperazine; 2-methylpiperazine; 2,5-dimethylpiperazine; 2,3,5,6-tetramethylpiperazine; 2-ethylpiperazine; 2,5-diethylpiperazine; 1,2-diaminoethane; 1,3-diaminopropane; 1,4-diaminobutane; 1,5-diaminopentane; 1,6-diaminohexane; 1,8-diaminooctane; 1,10-diaminodecane; 1,12-diaminododecane; N,N'-dimethyl-1,2-diaminoethane; N-methyl-1,3-diaminopropane; N-ethyl-1,2diaminoethane; N-isopropyl-1,2-diaminoethane; N-(2-hydroxyethyl)-1,2-diaminoethane; N,N'-bis(2-hydroxyethyl)-1,2-diaminoethane; N-(2-hydroxyethyl)-1,3-diaminopropane; N-hexenyl-1,6-diaminohexane; N,N'-diethyl-1,4-diamino-2-butene; 2,5-diamino-3-hexene; 2-aminoethylether; (2-aminoethoxy)methylether, 1,2 -bis(2-aminoethoxy)ethane; 1,3-diaminobenzene; 1,4-diaminobenzene; 2,4-diaminotoluene; 2,4-diaminoanisole; 2,4-diaminophenol; 4-aminophenylether; 4,4'-methylenedianiline, 4,4'-diaminobenzanilide; 3-aminophenylsulfone; 4-aminophenylsulfone; 4-aminophenylsulfoxide; 4-aminophenyldisulfide; 1,3-bis(aminomethyl)benzene; 1,4-bis(aminomethyl)benzene; 1,3-bis(aminomethyl)cyclohexane; 1,8-diamino-p-menthane; 1,4-bis(2-aminoethyl)piperazine; 1,4-bis(3-aminopropyl)piperazine; 1,4-bis(4-aminobuthyl)piperazine; 1,4-bis(5-aminopentyl)piperazine; etc..

Examples of polyvalent radicals:

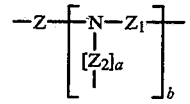

are those obtained from the following polyamino compounds by eliminating one hydrogen atom from any reacted amino group: bis(2-aminoethyl)amine; bis(3-aminopropyl)amine; bis(4-aminobuthyl)amine; bis(5-aminopentyl)amine; bis[2-(N-methylamino)ethyl]amine; 2-N-buthyl bis(2-aminoethyl)amine; bis [3-(N-methylamino)propyl]amine; N-(3-aminopropyl)-1,4-diaminobutane; N-(3-aminopropyl)-1,5-diaminopentane; N-(4-aminobuthyl)-1,5-diaminopentane; tris(2-aminoethyl)amine; tris(3-aminopropyl)amine; tris(4-aminobuthyl)amine; tris[2-(N-ethylamino) ethyl]amine; N,N'-bis(2-aminoethyl)-1,2-diaminoethane; N-N'-bis(3-aminopropyl)-1,3-diaminopropane; N,N'-bis(2-aminoethyl)-1,3-diaminopropane; N-N'-bis(3-aminopropyl)-1,2-diaminoethane; N,N'-bis(3-aminopropyl)-1,4-diaminobutane; bis[2-(2-aminoethyl)aminoethyl]amine; N,N'-bis[2-(2-aminoethyl)aminoethyl]-1,2-diaminoethane; N,N'-bis[3-(2-aminoethyl)aminopropyl]-1,2 -diaminoethane; N,N,N',N'-tetrakis(2-aminoethyl)-1,2-diaminoethane; etc.

Examples of phosphorus containing acids are: hypophosphorous acid; phosphorous acid; phosphoric acid;

pyrophosphoric acid; tripolyphosphoric acid; ethane-1,1,2-triphosphonic acid; 2-hydroxyethane-1,1,2-triphosphonic acid; propane-1,2,3-triphosphonic acid; isopropylphosphoric acid; n-buthylphosphoric acid; di-isoprylphosphoric acid; d-n-butyl phosphoric acid; di-n-pentylphosphoric acid; isooctylphosphoric acid; hexylphosphoric acid; 2-ethylhexylphosphoric acid; methylphosphonic acid; ethylphosphonic acid; n-propylphosphonic acid; n-buthylphosphonic acid; aminomethylphosphonic acid; phenylphosphoric acid; phenylphosphonic acid; phenylphosphinic acid; di-n-buthylpyrophosphoric acid; di(2-ethylhexyl)pyrophosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)ethane-1,1-diphosphonic acid; N,N-dimethylaminomethane-1,1-diphosphonic acid N-buthylaminomethane1,1-diphosphonic acid; phosphonacetic acid; 2-phosphonopropionic acid; 3-phosphonopropionic acid; 2-phosphonobutyric acid; 4-phosphonobutyric acid; 2-hydroxy-5,5-dimethyl-2-oxo-1,3,2-dioxophosphorinane; 3,9-dihydroxy-2,4,8,10-tetraoxo-3,9-diphosphaspyro[5,5]undecano-3,9-dioxyde; amino-tris(methylenphosphonic) acid; ethylendiaminotetra(methylenphosphonic) acid; examethylendiaminotetra(methylenphosphonic)acid; diethylentriaminopenta(methylenphosphonic) acid; etc.

Specific compounds included in the formula (I) are indicated in the examples which follow.

The products having the general formula (I) can be synthesized by reacting n moles of a polycondensate of 2,4,6-triamino-1,3,5-triazine, having the general formula (XIV):

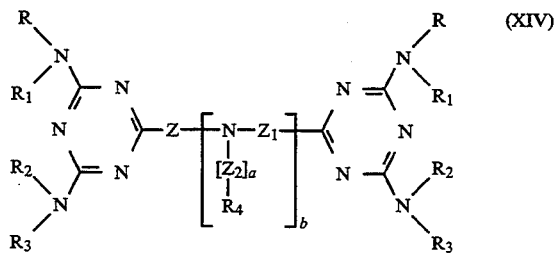

where n and the substituents from R to $R_3$, $R_4$ and the radical:

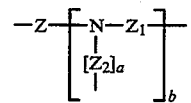

have the previously defined meaning, with one mole of an acid containing phosphorous of general formula (XV):

where $R_5$ and $R_6$ have the previously defined meaning, in the presence of a suitable solvent (for example water, methyl alcohol, ethyl alcohol, acetonitrile, etc.) at a temperature comprised between 0° C. and the boiling point of the solvent used, or without any solvent and with an excess of acid containing phosphorous, if the latter is able to act as a solvent, at a temperature comprised between 0° and 150° C.

The saline product obtained can be easily separated from the raction mass either by filtration or by distillation of the solvent.

Good quality products of general formula (I) are generally obtained in white, crystalline powder form, which can be used in self-extinguishing polymeric compositions without further purification.

Some of the intermediate products of general formula (XIV) are known; however, they can be easily synthesized according to the general method outlined herebelow:

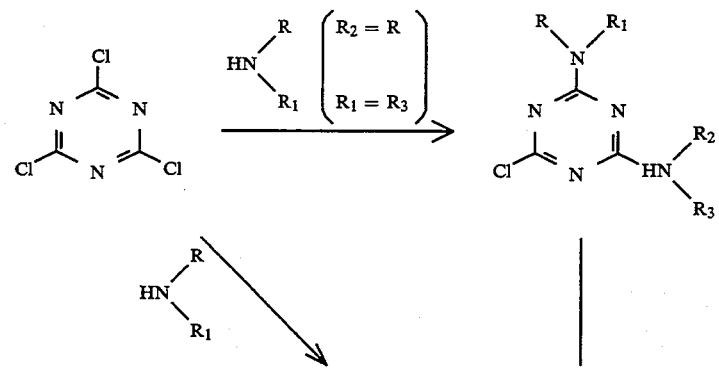

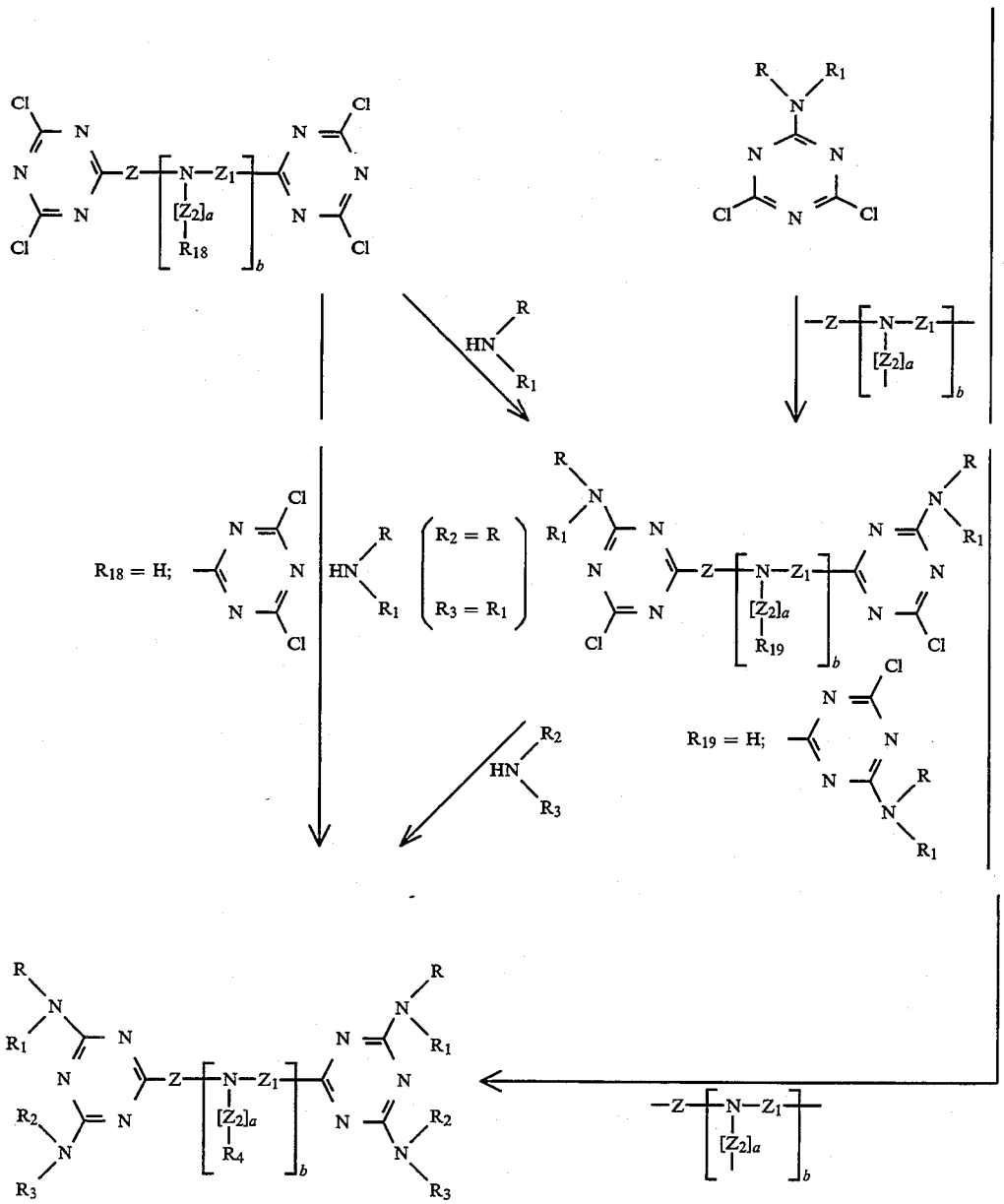

or as described in Italian patent applications n. 21562 A/89 of 28.08.89 and n. 18839 A/90 of 27.03.90, filed by the Applicant.

The acids containing Phosphorus of general formula (XV) are also known and many of them are available in commercial amounts.

The present invention, moreover, concerns self-extinguishing polymeric compositions including:

a) from 90 to 40 parts by weight of a thermoplastic polymer or a polymer having elastomeric properties;

b) from 10 to 60 parts by weight, preferably from 12 to 40, of one or more polycondensate compounds of 2,4,6-triamino-1,3,5-triazine salified with an oxygenated acid of phosphorus, said derivatives of 2,4,6-triamino-1,3,5-triazine having the general formula (XIV):

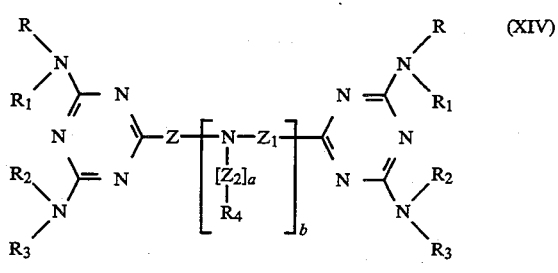

where:

the substituents from R to $R_3$, $R_4$ and the radical:

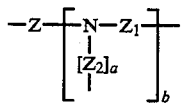

have the previuosly defined meaning.

The component (b) is preferably chosen among the salts having the general formula (I):

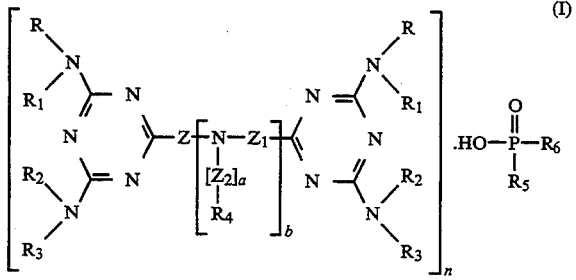

where:

n and the radicals from $R$ to $R_6$ and the substituent:

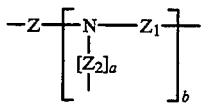

have the previously defined meaning.

It is particularly preferable to use the salts of compounds having the general formula (I) in which one or two of the groups:

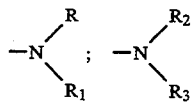

are substituted by a $NH_2$ radical.

If we want to further increase the self-extinguishing properties of polymeric compositions of the present invention, from 1 to 25 parts by weight of one or more ammonium and/or amine phosphates and/or phosphonates may be added to them, in place of an equal number of parts by weight of component (b).

Among the phosphates which can be used in addition to component (b) it is preferable to use ammonium polyphosphates which are included in the products of general formula $(NH_4)_{n+2}P_nO_{3n+1}$ where n represents an integer equal or higher than 2; the molecular weight of the polyphosphates should preferably be sufficiently high as to guarantee a low solubility in water, i.e. n should preferably vary between 2 and 500.

The composition of polyphosphates having the above-mentioned formula, where n is a sufficiently high number, preferably between 5 and 500, practically corresponds to the formula of methaphosphates $(NH_4PO_3)_n$.

An example of these polyphosphates is that known under the trade name of "Exolit 422" (produced and sold by Hoechst), having the composition $(NH_4PO_3)_n$ where n is higher than 50; another example is the product known under the trade-name "Phos-Chek P/30" (Monsanto Chemical) having similar composition.

Another polyphosphate which can be advantageously used, especially because of its low solubility in water, is that known under the trade name of "Exolit 462" (produced and sold by Hoechst) corresponding to Exolit 422 micro incapsulated in melamine-formaldehyde resin.

Other phosphates which can be used are those deriving from amines, for example dimethylammonium or diethylammonium phosphate, ethylenediamine phosphate, melamine ortho or pyrophosphate.

Among the polymers which can be used in the compositions of the present invention, polymers or copolymers of olefines having the general formula $R—CH=CH_2$ are preferred, where R is a hydrogen atom or a $C_1-C_8$ alkyl or aryl radical, in particular:

1. isotactic, or prevailingly isotactic polypropylene;
2. HDPE, LLDPE and LDPE;
3. crystalline copolymers of propylene with lower proportions of ethylene and/or other alpha-olefins, such as 1-butene, 1-hexene, 1-octene, 4-methyl-1-pentene;
4. heterophasic compositions including (A) a homopolymeric fraction of propylene or one of the copolymers indicated in point (3), and (B) a copolymeric fraction composed of elastomeric copolymers of ethylene with an alpha-olefin, optionally containing lower proportions of a diene, where the alpha-olefin is preferably chosen between propylene and 1-butene;
5. elastomeric copolymers of ethylene with alpha-olefins optionally containing a lower proportion of a diene. Examples of diene compounds which are most commonly present in the above elastomeric copolymers, are butadiene, ethylidene-norbornene, hexadiene 1-4. Among the polymers of olefins having the formula $R—CH=CH_2$ where R is an aryl radical, crystal and shock-resistant polystyrene are preferred.

Other examples of polymers commonly used are ABS terpolymers and SAN copolymers; polyurethane (polyester and polyether); polyethyleneterephthalate; polybutyleneterephthalate; polyamides; etc.

The self-extinguishing compositions of the present invention can be prepared using known methods: for example, the ammonium and/or amine phosphate, if used, is first carefully mixed with one or more salts of the general formula (I), finely ground, (preferably with particle size lower than 70 microns) and the mixture thus obtained is then added to the polymer in a turbo mixer forming a homogeneous mixture which is extruded and granulated. The granular product thus obtained can be transformed into various manufactures using one of the well-known molding techniques.

The flame-resistant additives of the present invention are also suitable for use in the field of antifire paints.

EXAMPLES

The following examples illustrate the characteristics of the invention without limiting them in any way.

The salification reactions between the intermediate products having the general formula (XIV) and the acids containing phosphorous having the general formula (XV) are confirmed by the IR spectroscopy analysis using a Perkin Elmer 580 B IR spectrophotometer.

It was observed, in fact, that an excellent reference signal is given by the peak caused by the deformation outside the triazine ring plane: the triazine ring gives a peak at approximately 830–800 $cm^{-1}$, whereas when the ring is salified on the amino-groups, the peak moves to 795-760 cm$^{-1}$.

EXAMPLE 1

184.5 g of cyanuric acid chloride and 1300 ml of methylene chloride are charged into a 3 liters reactor equipped with an agitator, thermometer, loading funnel, reflux condensing system and cooling bath.

At the same time, 75 g of 2-methoxyethylamine and 40 g of sodium hydrate dissolved in 150 ml of water are charged, during an external cooling, for a period of 3 hours, the pH being maintained at between 5 and 7 and the temperature between 0° and 3° C.

The whole mixture is kept at a temperature of 0°-3° C. for a further 3 hours and then the water phase is separated.

The organic solution is treated with two quantities of 200 ml each of water, and the water phase is separated each time.

217.5 g of the intermediate product (XVI):

(XVI)

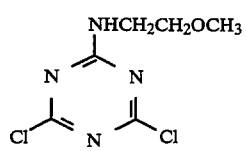

are obtained by the distillation of the methyl chloride, as a white, crystalline powder having m.p.=73°-75° C. (m.p.=melting point) and chlorine content equal to 31.68% (theoretical value: 31.84%).

400 ml of acetone and 133.8 g of the intermediate product (XVI) are charged into a 1 liter reactor equipped with an agitator, thermometer, loading funnel, reflux condenser and heating bath.

The mixture is stirred and heated to 40° C. until a solution is obtained, 102 g of a solution of ammonia at a concentration of 30% by weight, are then added over a period of 30 minutes during which the temperature is kept at 40° C.

The temperature is then raised to 45° C. and kept as such for 4 hours.

After it has been cooled to 10° C. the resulting cake is filtered and washed on the filter with cold water.

After drying i n an oven at 100° C., 114 g of the intermediate product (XVII):

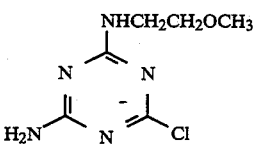

(XVII)

are obtained as a white crystalline powder having a m.p.=195°-197° C. and chlorine content equal to 17.18% (theoretical 17.44%).

The structure of the intermediate products (XVI) and (XVII) was confermed by IR spectroscopic analysis.

500 ml of xylene, 81.4 g of the intermediate product (XVII) and 17.2 g of piperazine are charged into the same 1 liter reactor.

The mixture is heated to 100° C. and this temperature is maintained for 2 hours.

16 g of sodium hydrate are then charged and the mixture is brought to the boiling temperature. It is kept under reflux for approx. 20 hours, then is cooled to room temperature and filtered.

The cake is washed adequately with water and dried.

74.2 g of the intermediate product (XVIII):

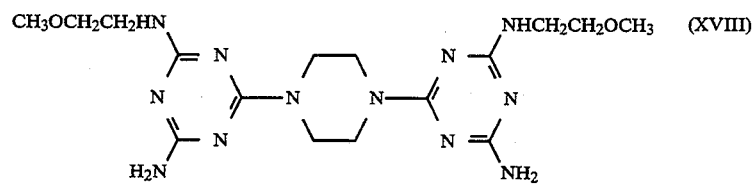

(XVIII)

are obtained, having a m.p.=212°-215° C.

63 g of the intermediate product (XVIII), plus 400 ml of acetonitrile and, under agitation, 34.6 g of a 85% by weight phosphoric acid are charged into the same 1 liter reactor.

The above mixture is heated to the boiling temperature and is kept under reflux for 8 hours.

After cooling to room temperature, the resulting cake is filtered and washed on the filter with acetonitrile.

After the cake has been dried in an oven at 100° C., 89.2 g of product:

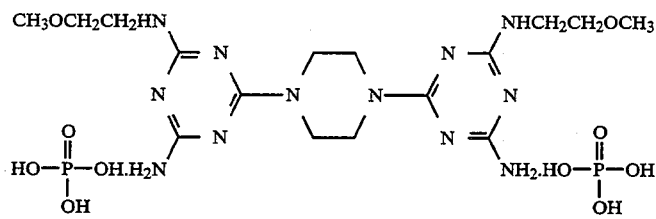

are obtained as a white crystalline powder having a m.p.=265°-268° C. and phosphorus content of 9.97% (theoretical: 10.06%).

EXAMPLE 2

84.5 g of cyanuric acid chloride and 1300 ml of methylene chloride are charged into the same 3 liters reactor of example 1.

With the same procedure as in example 1, but using 87.2 g of morpholine, 230 g of the intermediate product (XIX):

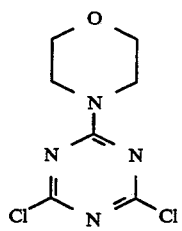

are obtained as a white, crystalline powder having a m.p.=155°–157° C. and a chlorine content of 29.87% (theoretical: 30.21%).

100 g of a 30% by weight solution of ammonia, 100 ml of water and 70.5 g of the intermediate product (XIX) are charged into a 0.5 liter reactor, equipped as in example 1.

The above mixture is heated to 50° C. and kept at this temperature for 7 hours. It is left to cool to room temperature and the resulting product is filtered and washed with water.

Upon drying of the compound, 58 g of the intermediate product (XX):

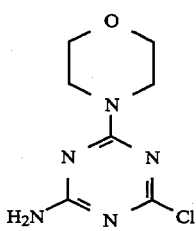

are obtained as a white, crystalline powder having a m.p.=189°–191° C. and a chlorine content of 16.28% (theoretical: 16.47%).

The structure of the compounds (XIX) and (XX) was confirmed by IR spectroscopic analysis.

400 ml of ortho-dichlorobenzene, 53.9 g of intermediate product (XX) and 14.5 g of hexamethylenediaine are charged into a 1 liter reactor equipped as above described.

The mixture is heated to 100° C. and kept at this temperature for 2 hours. 10 g of sodium hydrate are then added and the mixture is heated to 140° C. It is kept at this temperature for 16 hours, then is cooled to room temperature and the resulting product is filtered and washed thoroughly with water.

After drying, 62.3 g of the intermediate product (XXI):

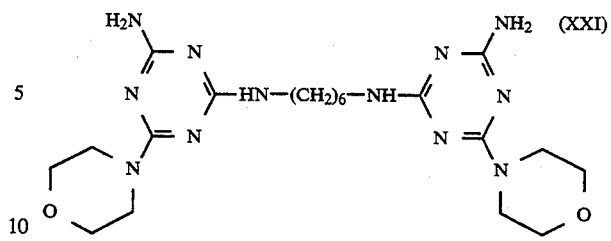

are obtained as a white, crystalline powder having a m.p.=267°–269° C.

300 ml of acetonitrile, 47.4 g of the intermediate product (XXI) and, under agitation, 24.2 g of a 85% by weight phosphoric acid are charged into a 0.5 liter reactor equipped as the above.

The mixture is heated to the boiling temperature and is kept under reflux for 12 hours.

After cooling to room temperature the resulting product is filtered and washed on the filter with acetonitrile.

After drying, 65.8 g of the product:

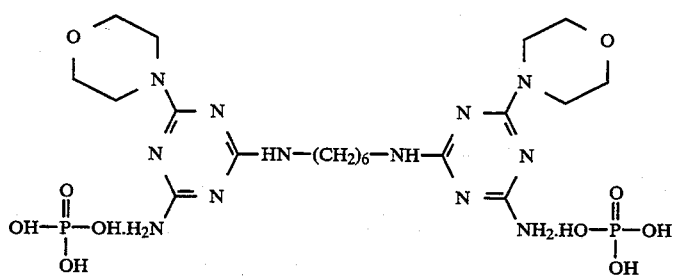

are obtained, as a white, crystalline powder having a m.p.=265°–268° C. and phosphorus content of 9.18% (theoretical: 9.25%).

EXAMPLE 3

184.5 g of cyanuric acid chloride and 800 ml of acetone are charged into a 3 liters reactor equipped with an agitator, thermometer, loading funnel, reflux condenser and heating bath.

The mixture is heated under agitation to 40° C. until a solution is obtained, and 284 g of a 30% by weight solution of ammonia are then added over a period of 30 minutes during which the temperature is maintained at 40° C.

It is then further heated to 45° C. and kept at this temperature for 4 hours.

After cooling, the resulting product is filtered and washed on the filter with water.

After drying under vacuum, in an oven at 50°–60° C., 113 g of the intermediate product (XXII):

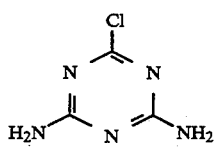

are obtained as a white, crystalline powder, having a m.p. higher than 300° C. and a chlorine content of 24.2% (theoretical: 24.4%).

The structure of the compound was confirmed by IR spectroscopic analysis.

400 ml of xylene, 58.2 g of the intermediate product (XXII) and 17.2 g of piperazine are charged into a 1 liter reactor equipped as above.

The mixture is heated to 100° C. and kept at this temperature for 2 hours.

16 g of solid sodium hydrate are then charged and the mixture brought to boiling temperature.

It is kept under reflux for about 20 hours, then cooled to room temperature and filtered.

The cake is washed thoroughly with water and dried. 54.2 g of the intermediate product (XXIII):

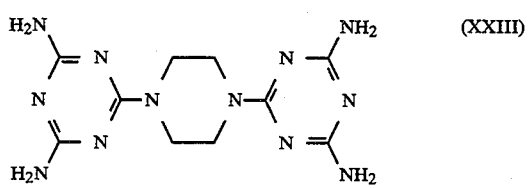 (XXIII)

are obtained as a white, crystalline powder having a m.p. higher than 300° C.

328 g of phosphorous acid and 82 g of acetonitrile are charged into a 1 liter reactor equipped as above.

The reaction mixture is slowly heated over a period of 6 hours to 160° C.

A white, crystalline powder is obtained.

It is then cooled to 80° C., 500 ml of water are added under strong agitation and the whole mixture is left to cool to room temperature.

The resulting product is separated by filtration and washed on the filter with a small amount of water.

After the cake has been dried, 290 g of 1-aminoethane-1,1-diphosphonic acid are obtained as a white, crystalline powder having a m.p.=265°–270° C. (with decomposition) and a phsphorus content of 29.4% (theoretical: 30.24%).

600 ml of water and 45.6 g of the intermediate product (XXIII) are charged into the same 1 liter reactor.

The mixture is heated to 80° C. and 61.6 g of 1-aminoethane-1,1-diphosphonic acid are charged under agitation.

It is brought to the boiling temperature and is maintained under reflux for approx. 8 hours.

It is then cooled to room temperature and the resulting product is filtered and washed on the filter with water.

After drying the cake, 102.5 g of the product:

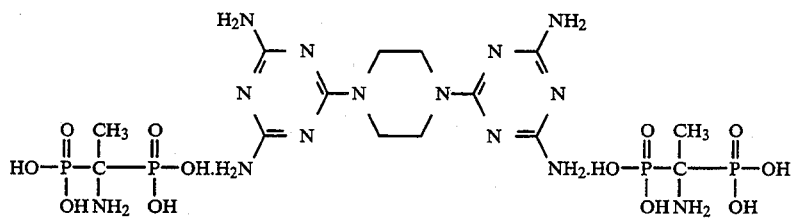

are obtained as a white, crystalline powder having a m.p.=273°–275° C. and a phosphorus content of 16.97% (theoretical: 17.36%).

EXAMPLE 4

600 ml of xylene, 107.8 g of the intermediate product (XX) and 15 g of ethylenediamine are charged into a 1 liter reactor equipped as in example 2.

With the same procedure as described in example 2, 99.6 g of the intermediate product (XXIV):

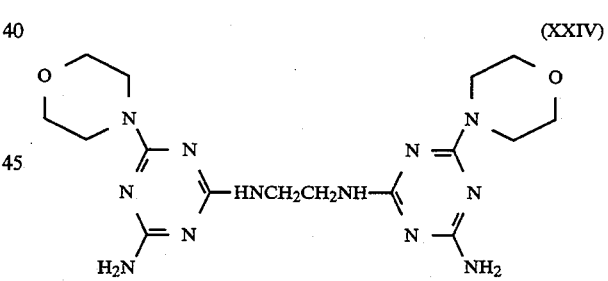 (XXIV)

are obtained as a white, crystalline powder having a m.p.=265°–268° C.

53.2 g of tetrasodium pyrophosphate and 400 ml of water are charged into the same 1 liter reactor, equipped with a cooling bath.

The mixture is cooled from the outside to 5° C. and 78.7 g of hydrochloric acid (37% by weight) are then added and a solution is obtained.

83.6 g of the intermediate product (XXIV) are added to this solution at a constant temperature of 5° C.

The above solution is then kept under agitation for 2 hours at the temperature of 5° C., is then left to reach room temperature and is kept under agitation for a further 3 hours.

It is again cooled to 2°–5° C. and the resulting product separated by filtration and washed on the filter with cold water.

After drying the cake, 108.1 g of the product:

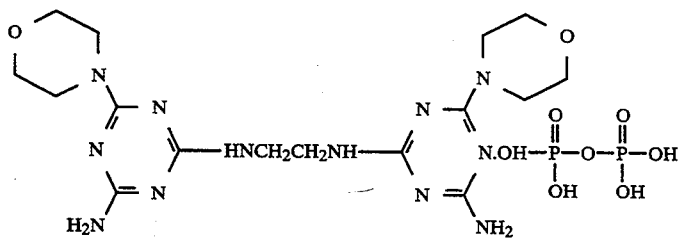

are obtained as a white, crystalline powder having a m.p.=277°-282° C. and phosphorus content of 9.97% (theoretical: 10.40%).

EXAMPLE 5

400 ml of xylene, 64.7 g of the intermediate product (XX) and 10.3 g of diethylenetriamine are charged into 1 liter reactor equipped as in the preceding examples.

The mixture is heated to 100° C. and kept at this temperature for 2 hours. 12 g of sodium hydrate are then added and the whole mixture is brought to boiling temperature.

The mass is maintained under reflux for 24 hours, is then cooled to room temperature and the resulting product is filtered and the cake is washed thoroughly with water.

After drying in an oven at 100° C., 56.7 g of the intermediate product (XXV):

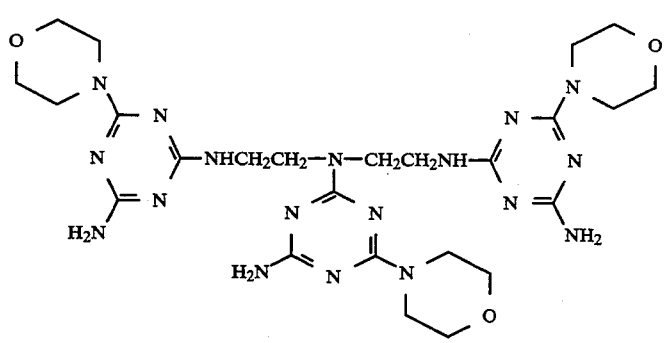

are obtained as a white, crystalline powder having a m.p.=207°-208° C.

150 ml of acetonitrile, 32.0 g of the intermediate product (XXV) and, under agitation, 18.2 g of phosphoric acid (85% by weight) are charged into a 0.5 liter reactor equipped as the above.

The mass is heated to boiling temperature and is maintained under reflux for 16 hours.

After cooling to room temperature, the resulting product is filtered and washed on the filter with acetonitrile.

After the cake is dried, 46.4 g of the product:

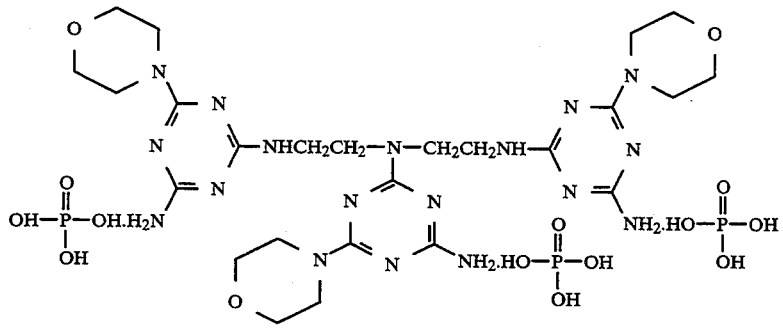

are obtained as a white, crystalline powder having a m.p.=99°-101° C. and phosphorus content of 9.77% (theoretical: 9.96%).

EXAMPLE 6

129 g of cyanuric acid chloride and 100 ml of methylene chloride are charged into a 2 liters reactor equipped as in the previous examples.

40 g of 3-amino-1-propene dissolved in 150 g of water are added to the solution kept at 0°-2° C. with external cooling, over a period of 90 minutes.

At a constant temperature of 0°-2° C. 28 g of sodium hydrate in 100 ml of water are added over a period of 2 hours. The solution is left under agitation for a further 2 hours at a temperature of 3°-5° C. and the water phase is then separated:

By distillation of the methylene chloride, 137 g of the intermediate product (XXVI):

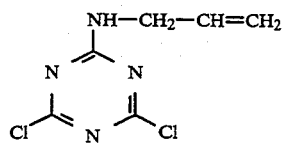

are obtained as a white, crystalline powder having a m.p.=70°-72° C. and a chlorine content of 34.37% (theoretical: 34.63%).

200 g of a 30% by weight of ammonia solution and 500 ml of water are charged into the same reactor and relevant equipment as above.

The solution is heated to 40° C. and 123 g of the intermediate product(XXVI) are added over a period of 30 minutes, the temperature being maintained at 40° C.

The temperature is raised to 45° C. and kept as such for approx. 6 hours.

After this period, the solution is cooled to room temperature and the resulting product filtered, washed with water and dried.

104 g of the intermediate product (XXVII):

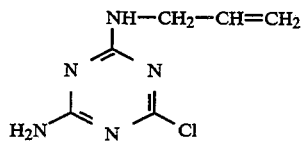

are obtained as a white, crystalline powder having a m.p.=168°-170° C. and chlorine content of 18.82% (theoretical: 19.14%).

The structures of the intermediate products (XXVI) and (XXVII) are confirmed by means of NMR analysis.

450 ml of xylene, 55.7 g of the intermediate product (XXVII) and 17.1 g of 2,5-dimethylpiperazine are charged into a 1 liter reactor equipped as above.

The mass is heated to 100° C. for 2 hours, then 12 g of solid sodium hydrate are added and it is brought to boiling temperature.

The mixture is kept under reflux for 18 hours and then the procedure is the same as in the previous examples.

56.3 g of the intermediate product (XXVIII):

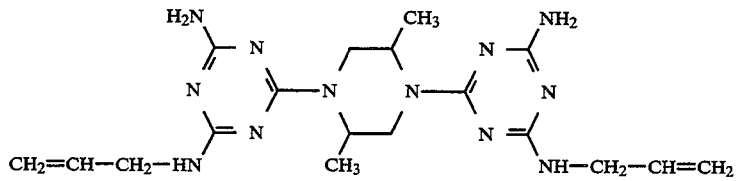

are obtained as a white, crystalline powder having a m.p.=192°-194° C.

400 ml of acetonitrile, 48.4 g of phosphoric acid (85% by weight) and, under agitation, 82.4 g of the intermediate product (XXVIII) are charged into the same 1 liter reactor.

It is then heated to boiling temperature and is kept under reflux for 10 hours.

The mixture is cooled to room temperature, the product obtained is filtered and is washed on the filter with acetonitrile.

After the cake has been dried 114.2 g of the product:

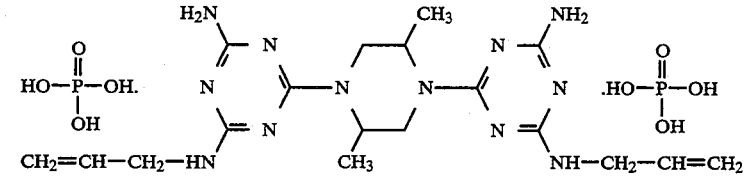

are obtained as a white, crystalline powder having a m.p.=197°-200° C. and phosphorus content of 9.87% (theoretical: 10.20%).

EXAMPLE 7

92.2 g of cyanuric acid chloride and 300 ml of acetone are charged into a 1 liter reactor equipped as in example 1.

21.5 g of piperazine dissolved in 200 ml of acetone are added to the mixture, over a period of 1 hour, with an external cooling to 0°-5° C.

20 g of sodium hydrate in 100 ml of water are added at the constant temperature of 0°-5° C.

The whole mixture is kept for further 4 hours under agitation at the temperature of 5° C. then 200 ml of cool water are added, the produced precipitate is filtered and is washed on the filter with water.

After drying, 88.7 g of the intermediate product (XXIX):

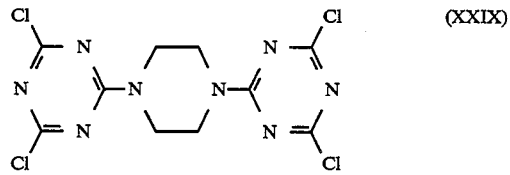

are obtained as a white, crystalline powder having a m.p. higher than 300° C. and chlorine content of 37.4% (theoretical: 37.2%).

The structure of the intermediate product (XXIX) is also confirmed by IR spectroscopic analysis.

400 ml of xylene and 76.4 g of the intermediate product (XXIX) are charged into the same 1 liter reactor equipped with the heating bath.

The mixture is heated to a temperature of 80° C. and then 60 g of 2-methoxyethylamine, followed by 32 g of sodium hydrate in 50 ml of water are added over a period of 4 hours.

The temperature is gradually raised and the water eliminated by means of azeotropic distillation until the boiling point of the solvent is reached.

The mixture is kept under reflux for 8 hours, then is cooled to room temperature, filtered and washed thorougly with water.

After drying, 93.2 g of the intermediate product (XXX):

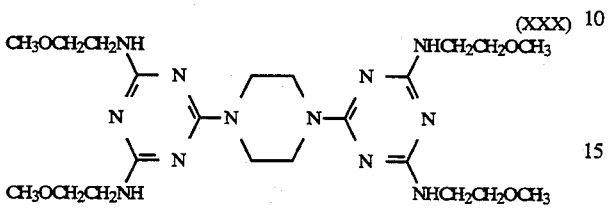

are obtained as a white, crystalline powder having a m.p.=170°-172° C.

400 ml of ethyl alcohol, 53.6 g of the intermediate product (XXX) and, under agitation, 24.2 g of phosphoric acid (85% by weight) are charged into the same 1 liter reactor.

The mixture is left under agitation at room temperature for approx. 14 hours, the resulting product is then filtered and is washed on the filter with a small amount of solvent.

By drying the cake in an oven at 100° C. 70.9 g of the product:

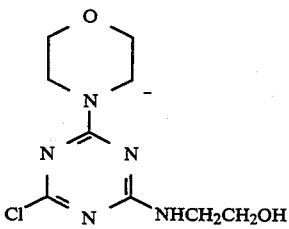

are obtained as a white, crystalline powder having a m.p.=168°-170° C. and a chlorine content of 13.59% (theoretical: 13.68%).

The structure of the intermediate product (XXXI) is also confirmad by means of NMR analysis.

400 ml of xylene, 77.9 g of the intermediate product (XXXI) and 12.9 g of piperazine are charged into a 1 liter reactor equipped as in the previous examples.

The mixture is heated to 100° C. for 2 hours, 12 g of solid sodium hydrate are then added and the whole mixture is brought to boiling temperature.

It is kept under a reflux for 16 hours, and the same procedure as described in the previous examples is then carried out.

65.4 g of the intermediate product (XXXII):

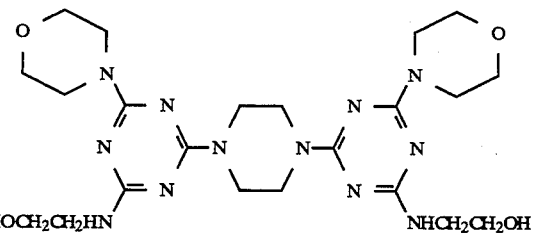

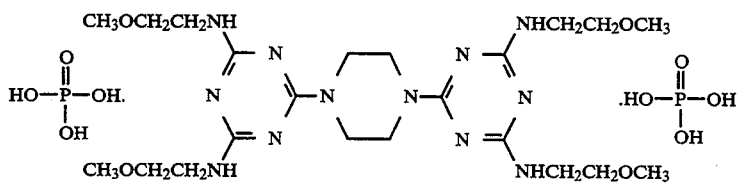

are obtained as a white, crystalline powder having a m.p.=242°-245° C. and a phosphorus content of 8.43% (theoretical: 8.47%).

EXAMPLE 8

400 ml of acetone, 500 ml of water and 94 g of the intermediate product (XIX) are charged into a 2 liter reactor equipped as in example 1.

The mixture is cooled from the outside to 5°-10° C. and then 49.8 g of 2-hydroxyethylamine are added over a period of 1 hour.

The temperature is raised to room temperature and the mixture left under agitation for 1 hour.

It is then heated to 40° C. and kept at this temperature for 2 hours.

It is again cooled to 10° C., the resulting product is filtered and washed with a small amount of cold water.

After drying the cake, 89.4 g of the intermediate product (XXXI):

are obtained as a white, crystalline powder having a m.p.=260°-262° C.

400 ml of acetonitrile, 53.2 g of the intermediate product (XXXII) and, under agitation, 16.8 g of phosphorous acid are charged into the same 1 liter reactor.

The mixture is brought to boiling point and kept under reflux for 8 hours.

It is cooled to room temperature, and the resulting product is filtered and washed on the filter with acetonitrile.

By drying the cake in an oven at 100° C. 68.9 g of the product:

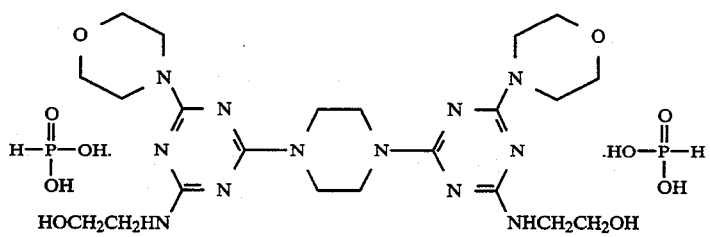

are obtained as a white, crystalline powder having a m.p.=176°-178° C. and a phosphorus content of 8.84% (theoretical: 8.91%).

EXAMPLE 9

500 ml of xylene, 86.2 g of the intermediate product

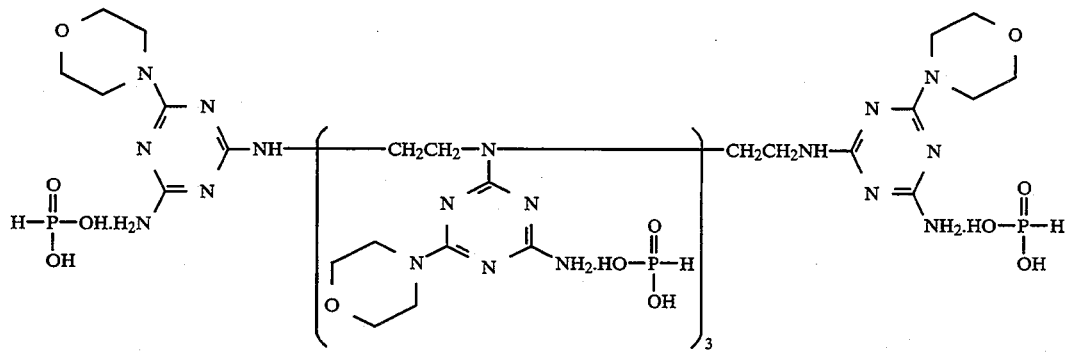

(XX) and 15.1 g of tetraethylenepentamine are charged into a 1 liter reactor equipped as in the previous examples.

The mixture is heated to 80° C. and is kept at this temperature for 2 hours.

16 g of sodium hydrate are then added and the temperature is raised to 110° C.

The mixture is kept at 110° C. for 18 hours, is then cooled to room temperature and the resulting product is filtered and washed thoroughly on the filter with water.

By drying the cake in an oven at 100° C. 82.6 g of the intermediate product (XXXIII):

The mixture is brought to boiling point and kept in a reflux condensing system for approx. 12 hours.

It is cooled to room temperature and the resulting product is filtered and washed on the filter with acetonitrile.

By drying in an oven, 72.7 g of the product:

are obtained as a white, crystalline powder having a m.p.=129°-132° C. and a phosphorus content of 10.61% (theoretical: 10.37%).

EXAMPLE 10

450 ml of water, 91.6 g of the intermediate product (XVII) and, under agitation, 21.9 g of tri(2-aminoethyl)amine are charged into a 1 liter reactor equipped as in the previous examples.

The mixture is heated to 80° C. and kept at this temperature for 3 hours.

18 g of sodium hydrate dissolved in 30 ml of water are

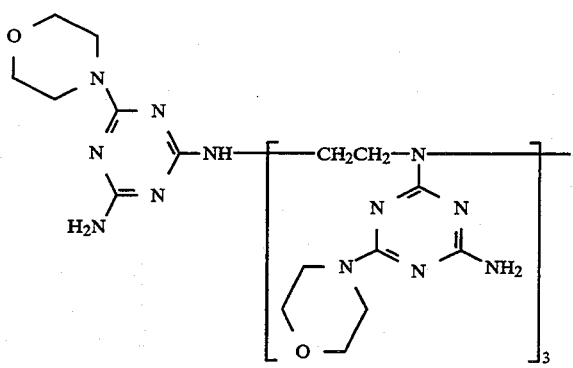 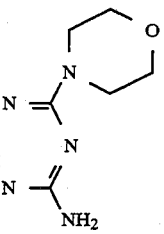

(XXXIII)

are obtained as a white, crystalline powder having a m.p.=178°-183° C.

350 ml of acetonitrile, 54.2 g of the intermediate product (XXXIII) and, under agitation, 20.5 g of phosphorous acid are charged into the same 1 liter reactor.

then added and the whole mixture is brought to boiling temperature.

It is kept under reflux for 16 hours, then is cooled to 10° C. and the resulting product is filtered and washed on the filter with cold water.

By drying the cake in an oven at 100° C., 85.4 g of the intermediate product (XXXIV):

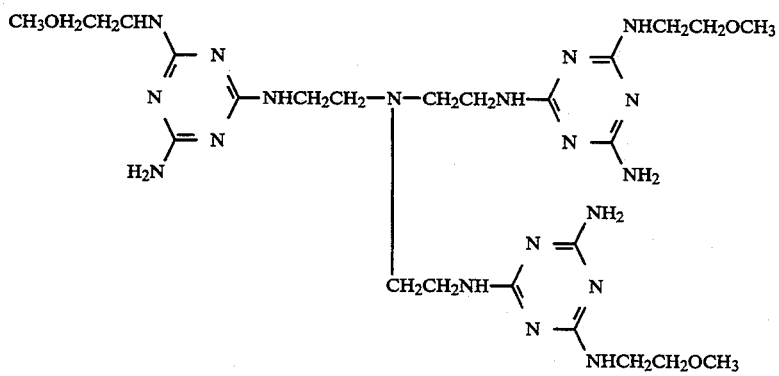

are obtained as a white, crystalline powder having a m.p. = 190°–195° C.

400 ml of acetonitrile, 64.7 g of the intermediate product (XXXIV) and, under agitation, 36.3 g of phosphoric acid (85% by weight) are charged into the same 1 liter reactor.

The mixture is heated to boiling temperature and is kept under reflux for approx. 14 hours.

the same 1 liter reactor with relevant equipment as described in the previous examples.

The mixture is heated to 80° C. for 2 hours, 16 g of sodium hydrate dissolved in 30 ml of water are then added and the whole mixture heated to boiling temperature.

It is kept under reflux for approx. 14 hours and the same procedure as described in the previous example is then carried out. 86.2 g of the intermediate product (XXXV):

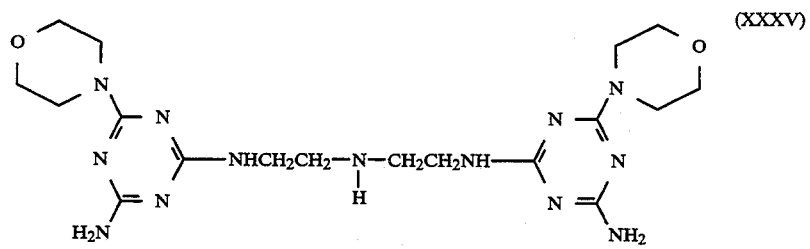

It is cooled to room temperature and the resulting product is filtered and washed on the filter with acetonitrile.

By drying the cake in an oven, 82.1 g of the product:

are obtained as a white, crystalline powder having a m.p. = 198°–201° C.

450 ml of acetonitrile, 69.1 g of the intermediate product (XXXV) and, under agitation, 36.3 g of phosphoric acid (85% by weight) are charged into the same 1 liter

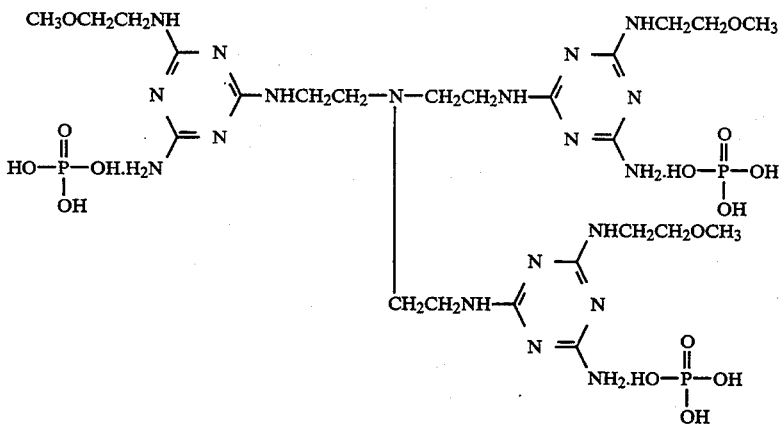

are obtained as a white, crystalline powder having a m.p. = 107°–111° C. and a phosphorus content of 10.15% (theoretical: 9.88% ).

EXAMPLE 11

400 ml of water, 86.2 g of the intermediate product (XX) and 20.6 g of diethylenetriamine are charged into reactor.

The mixture is heated to boiling temperature and kept under reflux for approx. 10 hours.

Using the same procedure as described in the previous example, 95.2 g of the product:

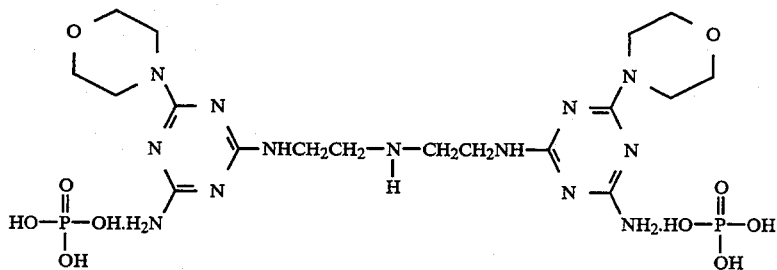
are obtained as a white, crystalline powder having a m.p.=120°–124° C. and a phosphorus content of 9.21% (theoretical: 9.44%).
EXAMPLES 12–52
The products having general formula (I) shown in Table 1 are synthesized under the same conditions as those described in examples 1–11.

TABLE 1

| ex. n. | R—N—R$_1$ | R$_2$—N—R$_3$ | $-Z-\left[N-Z_1\atop [Z_2]_a\right]_b$ | n | $HO-\underset{\underset{R_5}{\|}}{\overset{O}{\overset{\|}{P}}}-R_6$ | m.p. (°C.) | % phosphorus theoretical | % phosphorus experimental |
|---|---|---|---|---|---|---|---|---|
| 12 | cyclohexyl | H H | piperazine | 0,5 | H$_3$PO$_4$ | >300 | 9,34 | 9,12 |
| 13 | morpholine | H H | piperazine | 0,5 | pentaerythritol bis-phosphate | >300 | 9,75 | 9,48 |
| 14 | morpholine | H H | piperazine | 1 | H$_3$PO$_4$ | 272–277 | 5,71 | 5,58 |
| 15 | CH$_2$CH$_2$OCH$_3$ H | H H | piperazine | 0,5 | H$_3$PO$_4$ | 270–272 | 9,67 | 9,48 |
| 16 | CH$_2$CH$_2$OCH$_3$ H | H H | piperazine | 1 | aminomethylenediphosphonic acid | 206–210 | 9,90 | 9,57 |
| 17 | piperidine | H H | piperazine | 0,5 | aminomethylenediphosphonic acid | 235–240 | 14,92 | 15,18 |
| 18 | CH$_2$CH$_2$OCH$_3$ CH$_2$CH$_2$OCH$_3$ | H H | piperazine | 0,5 | H$_3$PO$_4$ | 260–263 | 9,75 | 9,52 |
| 19 | CH$_2$CH$_2$OCH$_3$ CH$_2$CH$_2$OCH$_3$ | H H | piperazine | 0,5 | H$_3$PO$_4$ | 155–160 | 8,79 | 8,54 |

TABLE 1-continued

| ex. n. | R—N—R₁ | R₂—N—R₃ | $-Z-\left[N-Z_1\atop[Z_2]_a\right]_b-$ | n | $HO-\overset{\overset{\displaystyle O}{\|}}{\underset{\displaystyle R_5}{P}}-R_6$ | m.p. (°C) | % phosphorus theoretical | % phosphorus experimental |
|---|---|---|---|---|---|---|---|---|
| 20 | morpholino | H, H | —HN—⟨C₆H₄⟩—NH— | 1 | methylenebis(phosphonic acid) with NH₂ (CH₃, C, NH₂, with two PO(OH)₂ groups) | 264–268 | 9,24 | 9,02 |
| 21 | H, H | H | piperazine (N—...—N) | 1 | CH₃—C(PO(OH)₂)₂—NH₂ type | 285–287 | 12,16 | 11,78 |
| 22 | morpholino | H | N(CH₂CH₂NH—)₃ | 0,33 | H₃PO₄ | 152–156 | 12,12 | 11,94 |
| 23 | morpholino | H | —HNC₂H₄[NC₂H₄]₃NH— | 0,33 | H₃PO₃ | 170–174 | 6,75 | 6,91 |
| 24 | morpholino | H | —HN—(CH₂)₆—NH— | 0,5 | $C_6H_5-\overset{\overset{O}{\|}}{P}(H)(OH)$ | 215–218 | 8,18 | 8,29 |
| 25 | H | H | —NCH₂CH₂NH—CH₂CH₂OH | 1 | H₃PO₄ | 194–198 | 5,54 | 5,49 |
| 26 | CH₂CH₂CH₂OC₂H₅ | H | —HN—⟨C₆H₄⟩—CONH—⟨C₆H₄⟩—NH— | 0,5 | H₃PO₄ | 218–221 | 7,63 | 7,91 |
| 27 | (CH₂)₅OH | H | piperazine (N—...—N) | 1 | pentaerythritol bis-phosphate (C(CH₂O)₄ with two P(O)(OH) cyclic) | 261–265 | 8,42 | 8,27 |

TABLE 1-continued

| ex. n. | R—N—R$_1$ | R$_2$—N—R$_3$ | $-Z-\left[\begin{array}{c}N-Z_1\\ \lfloor Z_2\rfloor_a\end{array}\right]_b$ | n | $\begin{array}{c}O\\ \|\|\\ HO-P-R_6\\ \|\\ R_5\end{array}$ | m.p. (°C.) | % phosphorus theoretical | experimental |
|---|---|---|---|---|---|---|---|---|
| 28 | (CH$_2$)$_3$OCH$_3$ | H | (CH$_2$)$_3$OCH$_3$ H | —NCH$_2$CH$_2$N—<br>   \|         \|<br>  CH$_3$      CH$_3$ | 0,5 | H$_3$PO$_4$ | 174–177 | 9,60 | 9,42 |
| 29 | CH$_2$CH$_2$OH | H | CH$_2$CH$_2$OH H | 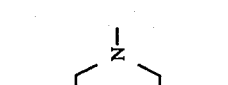 | | 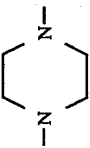 40%<br>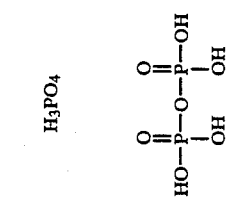 60% | 168–173 | 7,25 | 7,14 |
| 30 | CH$_2$CH$_2$OCH$_3$ | H | H | —HN—CH$_2$CH$_2$NCH$_2$CH$_2$NH— | 0,33 | H$_3$PO$_4$ | 285–290 | 10,36 | 10,11 |
| 31 | CH$_2$CH$_2$OCH=CH$_2$ | H | H | 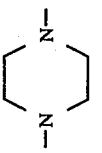 | 1 |  | 278–280 | 9,97 | 9,91 |
| 32 | (CH$_2$)$_2$O(CH$_2$)$_2$OH | H | H | 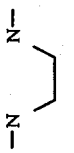 | 0,5 | H$_3$PO$_4$ | 177–181 | 9,17 | 8,95 |
| 33 | 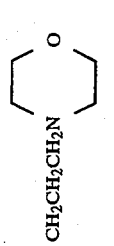 | H | H |  | 0,5 | H$_3$PO$_3$ | 201–204 | 8,59 | 8,38 |
| 34 | | | H | —HN—(CH$_2$)$_6$—NH | 0,5 | H$_3$PO$_4$ | 280–284 | 9,28 | 9,17 |

TABLE 1-continued

| ex. n. | R—N—R$_1$ | R$_2$—N—R$_3$ | $-Z-\left[\begin{array}{c}N-Z_1\\ {[Z_2]_a}\end{array}\right]_b-$ | n | $\begin{array}{c}O\\ \|\\ HO-P-R_6\\ \|\\ R_5\end{array}$ | m.p. (°C) | % phosphorus theoretical | % phosphorus experimental |
|---|---|---|---|---|---|---|---|---|
| 35 | CH$_2$CH$_2$OH, H | H, H | structure with cyclohexyl, C(CH$_3$)$_2$, NH, CH$_3$ | 1 | CH$_3$-C(NH$_2$)(PO$_3$H$_2$)$_2$ | 202–205 | 9,10 | 8,79 |
| 36 | morpholine, H | H, H | —HN—(CH$_2$CH$_2$O)$_2$—CH$_2$CH$_2$NH— | 0,5 | H$_3$PO$_4$ | 168–170 | 8,83 | 8,56 |
| 37 | morpholine, H | H, H | —HN—(CH$_2$)$_6$—NH— | 0,5 | H$_3$PO$_4$ | 195–196 | 9,70 | 9,62 |
| 38 | H, H | H, H | —HNCH$_2$-cyclohexyl-CH$_2$NH— | 1 | CH$_3$-C(NH$_2$)(PO$_3$H$_2$)$_2$ | 164–168 | 8,79 | 8,84 |
| 39 | H, H | H, H | piperazine | 1 | C$_{11}$H$_{23}$-C(NH$_2$)(PO$_3$H$_2$)$_2$ | 81–85 | 9,54 | 9,65 |
| 40 | H, H | H, H | piperazine | 1 | CH$_3$-C(NH$_2$)(PO$_3$H$_2$)$_2$ | 288–290 | 12,18 | 11,96 |
| 41 | H, H | H, H | piperazine | 1,5 | pyrophosphate diester | 291–294 | 13,02 | 12,91 |
| 42 | morpholine, H | H, H | —HN—(CH$_2$)$_6$—NH— | 1 | CH$_3$-C(NH$_2$)(PO$_3$H$_2$)$_2$ | 267–269 | 9,13 | 9,10 |

TABLE 1-continued

| ex. n. | R—N—R$_1$ | R$_2$—N—R$_3$ | $-Z-\left[-\underset{[Z_2]_a}{N-Z_1}-\right]_b$ | n | $\underset{R_5}{\overset{O}{\underset{\|}{HO-P-R_6}}}$ | m.p. (°C.) | % phosphorus theoretical | % phosphorus experimental |
|---|---|---|---|---|---|---|---|---|
| 43 | morpholine (N-linked) | H | piperazine | 1 | $\underset{HO}{\overset{O}{\underset{\|}{HO-P-}}}\underset{NH_2}{\overset{CH_3}{\underset{\|}{C}}}\underset{OH}{\overset{O}{\underset{\|}{P-OH}}}$ | 275–280 | 9,54 | 8,83 |
| 44 | morpholine (N-linked) | H | piperazine | — | phenyl-P(=O)(OH)$_2$ | 240–243 | 8,16 | 8,31 |
| 45 | CH$_2$=CH—CH$_2$ | H | piperazine | 0,5 | H$_3$PO$_4$ | 213–215 | 6,43 | 6,58 |
| 46 | H | H | piperazine | 1 | $\left[(CH_2)_2N\left[-CH_2\underset{OH}{\overset{O}{\underset{\|}{P-OH}}}\right]_2\right]-N-CH_2\underset{OH}{\overset{O}{\underset{\|}{P-OH}}}-\left[(CH_2)_2N\left[-CH_2\underset{OH}{\overset{O}{\underset{\|}{P-OH}}}\right]_2\right]$ | 203–206 | 11,63 | 11,50 |
| 47 | t-C$_8$H$_{17}$ | H | morpholine (N-linked) | —HN—(CH$_2$)$_6$—NH— | 0,5 | H$_3$PO$_4$ | 214–217 | 6,95 | 6,79 |

TABLE 1-continued

| ex. n. | R—N—R₁ | | R₂—N—R₃ | | $-Z-\left[\begin{array}{c}N-Z_1\\ [Z_2]_a\end{array}\right]_b$ | n | $\begin{array}{c}\text{O}\\ \parallel\\ \text{HO}-\text{P}-\text{R}_6\\ \vert\\ \text{R}_5\end{array}$ | m.p. (°C.) | % phosphorus theoretical | experimental |
|---|---|---|---|---|---|---|---|---|---|---|
| 48 | H | H | H | H | —N⌬N— (piperazine) | 0,5 | H₃PO₄ | 283–286 | 12,40 | 12,28 |
| 49 | morpholine | | H | H | —HNCH₂CH₂NH— | 0,5 | H₃PO₄ | 228–230 | 10,08 | 10,10 |
| 50 | morpholine | | H | H | —HNCH₂CH₂NCH₂CH₂NH— | 0,5 | H₃PO₄ | 188–191 | 7,42 | 7,23 |
| 51 | morpholine | | H | H | —HN(CH₂)₃N⌬N(CH₂)₃NH— | 0,5 | H₃PO₄ | 227–232 | 8,18 | 8,39 |
| 52 | H | H | H | H | —HNCH₂CH₂NCH₂CH₂NH— | 0,33 | H₃PO₄ | 232–235 | 12,84 | 12,69 |

Tables 2 and 3

The tests shown in the above tables refer to polymeric compositions containing products having general formula (I) prepared according to the previous examples.

Specimens were prepared, having a thickness of approx. 3 mm, by molding mixtures of granular polymer and additives in a MOORE plate press, operating for 7 minutes at a pressure of 40 kg/cm².

The self-extinguishing level was determined on the above specimens by measuring the oxygen index (L.O.I. according to ASTM D-2863/77)in a Stanton Redcroft equipment, and applying the "Vertical Burning Test" which allows to classify the material at three levels 94 V-0, 94 V-1 and 94 V-2 according to UL 94 codes (issued by "Underwriters Laboratories"—USA).

Table 2 shows the values obtained using isotactic polypropylene in flakes having a Melt Flow Index equal to 12 and an insoluble fraction in boiling n-eptane of 96% by weight.

Table 3 shows the values obtained using low density polyethylene in chips having a M.F.I. equal to 7; polystyrene in chips containing 5% by weight of butadiene rubber and having a M.F.I. equal to 9; thermoplastic polyurethane, both polyester (ESTANE 54600®) by Goodrich) and polyether (ESTANE 58300®) by Goodrich) in chips, having a specific weight equal to 1.19 and 1.10 g/ml respectively; an ethylene-propylene elastomeric copolymer having a 45% by weight content of propylene; an acrylonitrile-butadienestyrene terpolymer having a specific weight equal to 1.06 g/ml, a M.F.I. eual to 1.6 and containing approx. 40% of acrylonitrile and styrene and 20% of butadiene.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

TABLE 2

| ex-ample N. | product example N. | product | PP (1) | AO (2) | APP (1) | L.O.I. (ASTM D2863) | UL 94 3 mm |
|---|---|---|---|---|---|---|---|
| 53 | 1 | 13,5 | 72 | 1 | 13,5 | 33,2 | V0 |
| 54 | 2 | 34,0 | 65 | 1 | 0 | 31,0 | V0 |
| 55 | 2 | 11,5 | 76 | 1 | 11,5 | 36,3 | V0 |
| 56 | 3 | 12,0 | 75 | 1 | 12,0 | 34,1 | V0 |
| 57 | 4 | 34,0 | 65 | 1 | 0 | 30,9 | V0 |
| 58 | 5 | 23,2 | 70 | 1 | 5,8 | 32,4 | V0 |
| 59 | 6 | 12,5 | 74 | 1 | 12,5 | 34,7 | V0 |
| 60 | 7 | 39,0 | 60 | 1 | 0 | 30,7 | V0 |
| 61 | 8 | 21,6 | 72 | 1 | 5,4 | 33,7 | V0 |
| 62 | 9 | 35,0 | 64 | 1 | 0 | 32,1 | V0 |
| 63 | 9 | 16,0 | 75 | 1 | 8,0 | 33,9 | V0 |
| 64 | 10 | 34,0 | 65 | 1 | 0 | 30,8 | V0 |
| 65 | 11 | 34,0 | 65 | 1 | 0 | 31,6 | V0 |
| 66 | 12 | 13,5 | 72 | 1 | 13,5 | 34,9 | V0 |
| 67 | 13 | 35,0 | 64 | 1 | 0 | 31,8 | V0 |
| 68 | 14 | 12,0 | 74 | 1 | 13,0 | 33,2 | V0 |
| 69 | 15 | 36,0 | 63 | 1 | 0 | 31,0 | V0 |
| 70 | 16 | 22,0 | 66 | 1 | 11,0 | 31,3 | V0 |
| 71 | 17 | 39,0 | 60 | 1 | 0 | 29,9 | V0 |
| 72 | 18 | 15,0 | 69 | 1 | 15,0 | 32,7 | V0 |
| 73 | 19 | 18,0 | 72 | 1 | 9,0 | 33,5 | V0 |
| 74 | 20 | 23,2 | 70 | 1 | 5,8 | 31,8 | V1 |
| 75 | 21 | 12,0 | 75 | 1 | 12,0 | 32,7 | V0 |
| 76 | 22 | 12,0 | 75 | 1 | 12,0 | 33,4 | V0 |
| 77 | 23 | 34,0 | 65 | 1 | 0 | 32,4 | V0 |
| 78 | 24 | 19,0 | 70 | 1 | 10,0 | 31,5 | V0 |
| 79 | 25 | 13,0 | 73 | 1 | 13,0 | 32,8 | V0 |
| 80 | 26 | 23,2 | 70 | 1 | 5,8 | 30,7 | V1 |
| 81 | 27 | 34,0 | 65 | 1 | 0 | 31,2 | V0 |
| 82 | 28 | 25,8 | 70 | 1 | 3,2 | 32,1 | V0 |
| 83 | 29 | 18,0 | 72 | 1 | 9,0 | 31,7 | V0 |
| 84 | 30 | 14,0 | 75 | 1 | 10,0 | 32,9 | V0 |
| 85 | 31 | 39,0 | 60 | 1 | 0 | 30,9 | V1 |
| 86 | 32 | 36,0 | 63 | 1 | 0 | 30,1 | V0 |
| 87 | 33 | 23,2 | 70 | 1 | 5,8 | 34,2 | V0 |
| 88 | 34 | 13,0 | 73 | 1 | 13,0 | 33,4 | V0 |
| 89 | 35 | 13,5 | 72 | 1 | 13,5 | 32,6 | V0 |
| 90 | 36 | 35,0 | 64 | 1 | 0 | 30,2 | V0 |
| 91 | 37 | 20,0 | 70 | 1 | 9,0 | 32,4 | V0 |
| 92 | 38 | 14,5 | 71 | 1 | 13,5 | 33,6 | V0 |
| 93 | 39 | 14,5 | 70 | 1 | 14,5 | 29,4 | V1 |
| 94 | 40 | 10,5 | 78 | 1 | 10,5 | 32,1 | V0 |
| 95 | 41 | 39,0 | 60 | 1 | 0 | 30,9 | V1 |
| 96 | 42 | 35,0 | 64 | 1 | 0 | 31,8 | V0 |
| 97 | 43 | 39,0 | 60 | 1 | 0 | 31,2 | V0 |
| 98 | 43 | 16,0 | 75 | 1 | 8,0 | 30,5 | V0 |
| 99 | 44 | 13,0 | 73 | 1 | 13,0 | 31,1 | V0 |
| 100 | 45 | 13,5 | 72 | 1 | 13,5 | 30,2 | V1 |
| 101 | 46 | 39,0 | 60 | 1 | 0 | 32,0 | V0 |
| 102 | 47 | 14,5 | 71 | 1 | 13,5 | 32,3 | V0 |
| 103 | 48 | 12,0 | 75 | 1 | 12,0 | 32,7 | V0 |
| 104 | 49 | 9,6 | 75 | 1 | 14,4 | 35,9 | V0 |
| 105 | 50 | 12,0 | 75 | 1 | 12,0 | 36,1 | V0 |
| 106 | 51 | 20,0 | 72 | 1 | 7,0 | 32,8 | V0 |
| 107 | 52 | 13,5 | 72 | 1 | 13,5 | 32,6 | V0 |
| 108 | 3 | 16,0 | 75 | 1 | *8,0 | 32,5 | V0 |
| 109 | 15 | 16,0 | 75 | 1 | *8,0 | 33,6 | V0 |
| 110 | 42 | 19,3 | 70 | 1 | *9,7 | 37,4 | V0 |

(1) PP = Polypropylene
APP = ammonium polyphosphate - Exolit 422^R (Hoechst)
*APP microincapsulated in melamine-formaldehyde resin Exolit 462^R (Hoechst)
(2) AO = antioxidant.
Mixture consisting of 2 parts of dilauryltiopropyonate and 1 part of tetra [3-(3,5-diterbuthyl-4-hydroxyphenil) propionate] of pentaerythritol.

TABLE 3

| ex. n. | POLI MERIC SUPP. | PRODUCT EXAMPLE N. | POLYMER | PRODUCT | AO (2) | APP (1) | L.O.I. (ASTM-D2863) | UL94 3 mm |
|---|---|---|---|---|---|---|---|---|
| 111 | LDPE | 2 | 60 | 34,7 | 1 | 4,3 | 28,6 | V2 |
| 112 | (1) | 2 | 67 | 16,0 | 1 | 16,0 | 32,6 | V0 |
| 113 | | 3 | 70 | 14,5 | 1 | 14,5 | 32,8 | V0 |
| 114 | | 10 | 65 | 20,0 | 1 | 14,0 | 31,5 | V0 |
| 115 | | 15 | 66 | 16,5 | 1 | 16,5 | 32,8 | V0 |
| 116 | | 19 | 64 | 17,5 | 1 | 17,5 | 33,2 | V0 |
| 117 | HIPS | 3 | 70 | 15,0 | 1 | 14,0 | 31,7 | V0 |
| 118 | (1) | 5 | 71 | 15,0 | 1 | 13,0 | 32,4 | V0 |
| 119 | | 15 | 68 | 15,5 | 1 | 15,5 | 31,2 | V0 |
| 120 | PP/PE | 2 | 60 | 39,0 | 1 | 0 | 28,7 | V0 |
| 121 | (1) | 3 | 72 | 13,5 | 1 | 13,5 | 34,3 | V0 |
| 122 | | 30 | 70 | 23,2 | 1 | 5,8 | 31,4 | V0 |
| 123 | | 38 | 60 | 39,0 | 1 | 0 | 27,5 | V0 |
| 124 | PU | 1 | 70 | 29 | 1 | 0 | 31,4 | V0 |

TABLE 3-continued

| ex. n. | POLI MERIC SUPP. | PRODUCT EXAMPLE N. | PARTS BY WEIGHT POLYMER | PARTS BY WEIGHT PRODUCT | AO (2) | APP (1) | L.O.I. (ASTM-D2863) | UL94 3 mm |
|---|---|---|---|---|---|---|---|---|
| 125 | ether | 3 | 70 | 29 | 1 | 0 | 33,6 | V0 |
| 126 | (1) | 23 | 70 | 29 | 1 | 0 | 30,7 | V0 |
| 127 | PU | 1 | 70 | 29,0 | 1 | 0 | 33,7 | V0 |
| 128 | (ester) | 3 | 70 | 29,0 | 1 | 0 | 35,2 | V0 |
| 129 | (1) | 17 | 74 | 25,0 | 1 | 0 | 34,1 | V0 |
| 130 |  | 21 | 70 | 29,0 | 1 | 0 | 32,2 | V0 |
| 131 |  | 22 | 65 | 34,0 | 1 | 0 | 34,8 | V0 |
| 132 |  | 23 | 70 | 29,0 | 1 | 0 | 32,7 | V0 |
| 133 |  | 48 | 70 | 29,0 | 1 | 0 | 33,2 | V0 |
| 134 |  | 50 | 75 | 24,0 | 1 | 0 | 35,2 | V0 |
| 135 | ABS | 2 | 70 | 14,5 | 1 | 14,5 | 33,2 | V0 |
| 136 | (1) | 23 | 72 | 13,5 | 1 | 13,5 | 32,4 | V0 |

(1) APP = ammonium polyphosphate - Exolit 422$^R$ (Hoechst)
LDPE = low density polyethylene
HIPS = polystyrene with 5% of butadiene rubber
PU (ester) = polyurethane polyester
PU (ether) = polyurethane polyether
PP/PE = propylene/ethylene copolymer
ABS = acrylonitrile-butadiene-styrene terpolymer
(2) AO = antioxydant.
Mixture consisting of 2 parts of dilauryltiopropyonate and 1 part of tetra[3-(3,5-diterbuthyl-4-hydroxyphenil) propionate] of pentaerythritol.

EXAMPLE 137

For Comparison

With the same procedure used in the examples from 53 to 110, but making use of the 2,4,6-triamino-1,3,5-triazine phosphate (1:1) as nitrogen-containing compound, the following composition was prepared:

| | |
|---|---|
| Polypropylene: | 65 parts by weight |
| Antioxydant: | 1 part by weight |
| 2,4,6-triamino-1,3,5-triazine phosphate (1:1): | 34 parts by weight |

Specimens were prepared using the above composition and self-extinguishing tests carried out on these samples, according to the previously described procedure.
The following results were obtained:
L.O.I.=23.5
Ul 94 (3 mm)=class B (the specimen burns).

EXAMPLE 138

For Comparison

With the same procedure described in example 137, the following composition was prepared:

| | |
|---|---|
| Polypropylene: | 73 parts by weight |
| Antioxydant: | 1 part by weight |
| Ammonium polyphosphate: | 13 parts by weight |
| 2,4,6-triamino-1,3,5-triazine phosphate (1:1): | 13 parts by weight |

Specimens were prepared using the above composition and self-extinguishing tests carried out on these samples, according to the previously described procedure.
The following results were obtained:
L.O.I.=22.5
UL 94 (3 mm)=class B (the specimen burns).
We claim:
1. Self-extinguishing polymer composition comprising:

a) from 90 to 40 parts by weight of a thermoplastic polymer or of a polymer having elastomeric properties;

b) from 10 to 60 parts by weight of at least one polycondensate compound of 2,4,6-triamino-1,3,5-triazine salified with an oxygenated acid of phosphorus, said derivatives of 2,4,6-triamino-1,3,5-triazine having the formula (XIV):

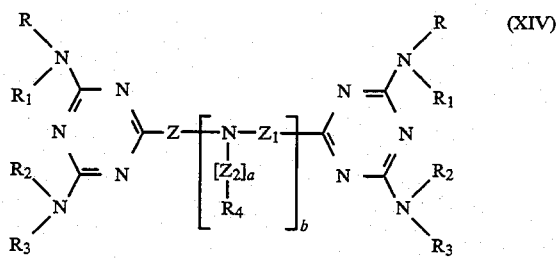

where:

the radicals from R to $R_3$, either alike or different, and which can also have different meanings for each triazine ring, are:

H; $C_1$-$C_{18}$ alkyl; $C_2$-$C_8$ alkenyl; $C_6$-$C_{16}$ cycloalkyl; or $C_6$-$C_{16}$ alkylcycloalkyl, optionally substitute with a hydroxyl or $C_1$-$C_4$ hydroxy alkyl group;

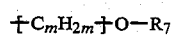

where m is an integer between 2 and 8 and $R_7$=H; $C_1$-$C_8$ alkyl; $C_2$-$C_6$ alkenyl; —O—$R_9$ were q is an integer between 1 and 4 and $R_9$ is H or $C_1$-$C_4$ alkyl; $C_6$-$C_{12}$ cycloalkyl or $C_6$-$C_{12}$ alkyl cycloalkyl;

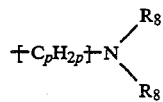

where p=an integer between 2 and 6 and the $R_8$ radicals, either alike or different, are:

H; $C_1$-$C_8$ alkyl; $C_2$-$C_6$ alkenyl; $C_6$-$C_{12}$ cycloalkyl or $C_6$-$C_{12}$ alkyl cycloalkyl; $C_1$-$C_4$ hydroxy alkyl; or —NR$_8$R$_8$ forms a heterocyclic radical selected from the group consisting of aziridine, pyrrolidine, piperidine, morpholine, thiomorpholine, piperazine, 4-methylpiperazine or 4-ethylpiperazine;

or at least one of the groups —NRR$_1$ or NR$_2$R$_3$ in the formula (I) forms a heterocyclic radical selected from the group consisting of aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine or 2,5-diethylpiperazine;

a is 0 or 1 b is 0 or an integer between 1 and 5;

R$_4$ is hydrogen or:

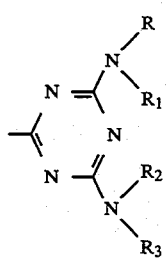

and its meaning can vary within each repetition unit; when b is 0, Z is a bivalent radical selected from one of the following formulae:

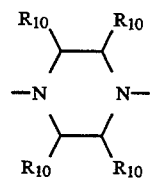 (II)

where the R$_{10}$ radicals, either alike or different, are hydrogen or C$_1$-C$_4$ alkyl:

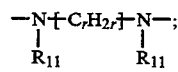 (III)

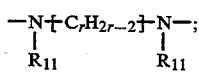 (IV)

where r is an integer between 2 and 14 and R$_{11}$ is hydrogen; C$_1$-C$_4$ alkyl; C$_2$-C$_6$ alkenyl; C$_1$-C$_4$ hydroxy alkyl;

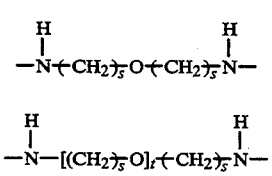

where s is an integer between 2 and 5 and t is an integer between 1 and 3;

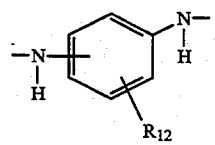 (VII)

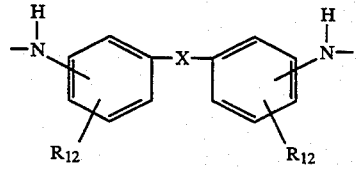 (VIII)

where: X is a C—C bond; O; S; S—S; SO; SO$_2$; NH; NHSO$_2$; NHCO; N=N; CH$_2$; and R$_{12}$ is hydrogen; a hydroxy radical; C$_1$-C$_4$ alkyl; or C$_1$-C$_4$ alkoxy;

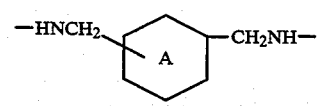 (IX)

where A can be a saturated or unsaturated cycle;

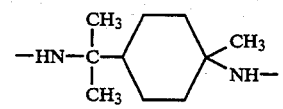 (X)

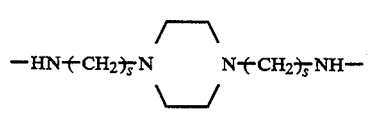 (XI)

where s has the previously defined meaning; when b is an integer between 1 and 5, the group:

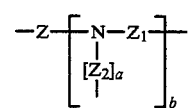

is a polyvalent radical selected from one of the following formulae:

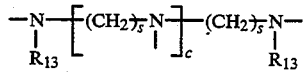 (XII)

where: R$_{13}$ is hydrogen or C$_1$-C$_4$ alkyl; c is an integer between 1 and 5; indexes s, either alike or different, have the above defined meaning;

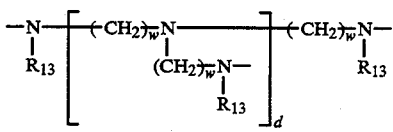 (XIII)

where: R$_{13}$ has the previously defined meaning; w is an integer between 2 and 4; d is either 1 or 2.

2. Self-extinguishing polymeric composition according to claim 1 wherein at least one of the groups:

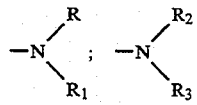

in the formula (XIV) is an heterocyclic radical selected from the group consisting of: aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; and 2,5-dimethylpiperazine.

3. Self-extinguishing polymeric composition according to claim 1 wherein at least one of the radicals from R to $R_3$ in the formula (XIV) is replaced by a group:

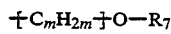

where m is an integer between 2 and 4 and $R_7$ is hydrogen or $C_1$-$C_4$ alkyl.

4. Self-extinguishing polymeric composition according to claim 1, wherein the group:

is a heterocyclic radical selected from the group consisting of: aziridine; pyrrolidine; piperidine; morpholine; thiomorpholine; piperazine; 4-methylpiperazine; and 4-ethylpiperazine.

5. Self-extinguishing polymeric composition according to claim 1, wherein at least one of the groups:

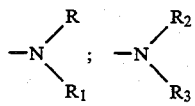

in the formula (XIV) is replaced by a $-NH_2$ group.

6. Self-extinguishing polymeric composition according to claim 1 wherein the composition includes:
from 90 to 40 parts by weight of component (a);
from 9 to 35 parts by weight of component (b); and
from 1 to 25 parts by weight of at least one ammonium and/or amine phosphate and/or phosphonates (c).

7. Self-extinguishing polymeric composition according to claim 6, wherein the ammonium phosphate or phosphates (c) have formula $(NH_4)_{n+2}P_nO_{3n+1}$ where n is an integer number equal to or greater than 2.

8. Self-extinguishing polymeric composition according to claim 6, wherein the ammonium phosphate or phosphates (c) have formula $(NH_4PO_3)_n$ where n is a number between 50 and 500.

9. Self-extinguishing polymeric composition according to claim 6, wherein the phosphate or the phosphates of amine (c) are selected from the group consisting of dimethylammonium or diethylammonium phosphate; ethylenediamine phosphate; and ortho or pyrophosphate of melamine.

10. Self-extinguishing polymeric composition according to claim 1, wherein the polymer (a) is selected from the group consisting of the polymers or copolymers of olefins having formula $R-CH=CH_2$ where R is a hydrogen atom or a $C_1$-$C_8$ alkyl or aryl radical; the acrylonitrile/butadiene/styrene terpolymers; the acrylonitrile/styrene copolymers; polyurethane; polyethyleneterephthalate; polybutyleneterephthalate; and polyamides.

11. Self-extinguishing polymeric composition according to claim 10, wherein the polymers and copolymers of olefins are selected from the group consisting of:
a. isotactic, or almost isotactic polypropylene;
b. HDPE, LLDPE and LDPE;
c. propylene crystalline copolymers with lower proportions of ethylene and/or other alpha-olefins, including 1-butene, 1-hexene, 1-octene, 4-methyl-1-pentene;
d. heterophastic compositions including (A) a homopolymeric fraction of propylene or one of the copolymers indicated in point c, and (B) a copolymeric fraction composed of elastomeric copolymers of ethylene with an alpha-olefin; and
e. elastomeric copolymers of ethylene with alpha-olefins possibly containing lower proportion of a diene.

12. Molded manufactures obtained from the composition of claim 1.

13. Self-extinguishing polymeric composition according to claim 11, wherein the alpha-olefin in (d) is propylene or 1-butene.

14. Self-extinguishing polymeric composition according to claim 11, wherein the alpha-olefin in (d) contains lower proportions of a diene.

15. Self-extinguishing polymeric compositions according to claim 1 wherein component (b) is selected from among the salts having the formula (I).

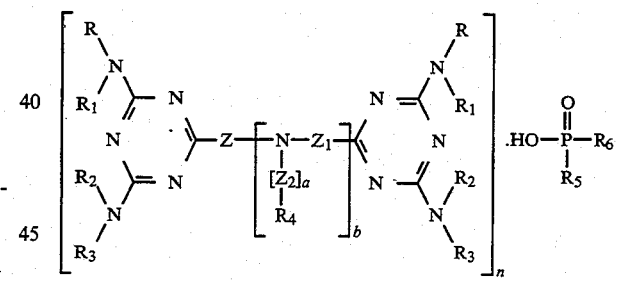

where:
the radicals from R to $R_4$ and the substituent:

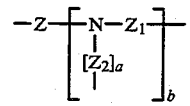

have the meaning defined in claim defined in claim 22 while
n is a number from greater than 0 to 3;
$R_5$ is H, OH, $-O-C_1-C_8$ alkyl; $-O-C_6-C_{12}$ aryl, optionally substituted with a $C_1-C_8$ alkyl; $C_7-C_{12}$ aralkyl, optionally substituted with a $C_1-C_4$ alkyl; $C_1-C_4$ alkyl, optionally substituted with a carboxylic group; $C_6-C_{12}$ aryl;
$R_6$ is H, OH, $-O-C_1-C_8$ alkyl; $-O-C_6-C_{12}$ aryl; $C_1-C_4$ alkyl; $C_6-C_{12}$ aryl;
$R_6$ is also

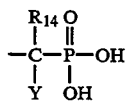

where: $R_{14}$ is H or $C_1$-$C_{12}$ alkyl; Y is OH or $R_{14}$;

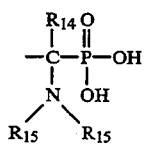

where: $R_{14}$ has the previously defined meaning, and the $R_{15}$ radicals, either alike or different, are H or $C_1$-$C_4$ alkyl;

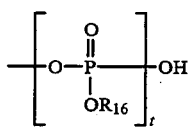

where: $R_{16}$ is H or $C_1$-$C_8$ alkyl; and t has the previously defined meaning;

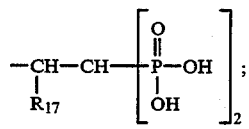

where: $R_{17}$ is H or OH;

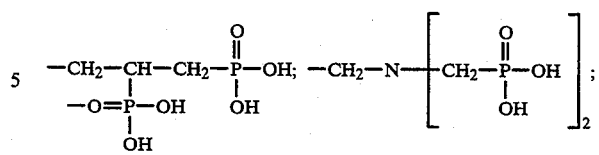

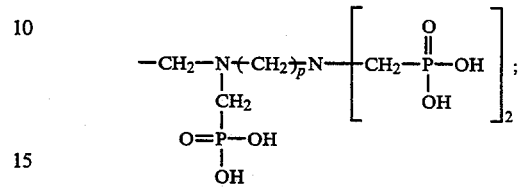

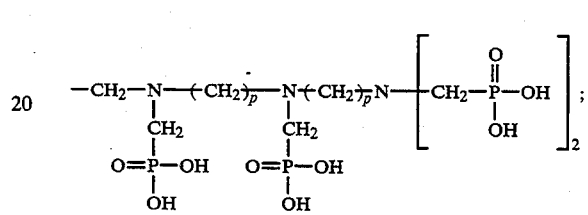

where: p has the previously defined meaning; or $R_5$ and $R_6$ together may form a cyclic structure having formula:

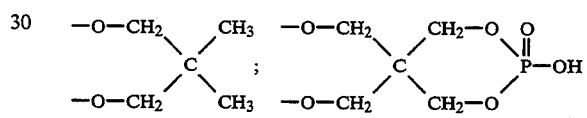

with the proviso that the bivalent or polyvalent radical, defined in claim 22, belongs to the formulae (II), (IV)-(XI) and (XIII), and the radicals $R_5$ and $R_6$, defined above, are different from H and OH respectively.

* * * * *